US012674853B2

(12) United States Patent (10) Patent No.: US 12,674,853 B2

Chance et al. (45) Date of Patent: *\*Jul. 7, 2026*

(54) METHOD OF OBTAINING AN INDICATION OF AN EFFICACY OF A DRUG

(71) Applicant: Oxford University Innovation Limited, Oxford (GB)

(72) Inventors: Steven Chance, Headington (GB); Rebecca McKavanagh, Headington (GB); Mark Jenkinson, Headington (GB); Karla Miller, Headington (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,858

(22) Filed: Sep. 13, 2023

(65) Prior Publication Data

US 2024/0069138 A1 Feb. 29, 2024

Related U.S. Application Data

(63) Continuation of application No. 17/115,129, filed on Dec. 8, 2020, now Pat. No. 11,796,619, which is a (Continued)

(30) Foreign Application Priority Data

Apr. 8, 2015 (GB) .................................... 1505940

(51) Int. Cl.
*G01R 33/563* (2006.01)
*A61B 5/00* (2006.01)

(Continued)

(52) U.S. Cl.
CPC ........ *G01R 33/56341* (2013.01); *A61B 5/055* (2013.01); *A61B 5/4088* (2013.01); *A61B 2576/026* (2013.01); *G01R 33/5608* (2013.01)

(58) Field of Classification Search
CPC .......... G01R 33/56341; G01R 33/5608; A61B 5/055; A61B 5/4088; A61B 2576/026; G16H 30/40
See application file for complete search history.

(56) References Cited

U.S. PATENT DOCUMENTS 7,006,859 B1 2/2006 Osorio et al.
7,903,251 B1 3/2011 Farr et al.
(Continued)

FOREIGN PATENT DOCUMENTS

JP 3581319 B2 * 10/2004 ......... A61B 5/04008
WO 2013/040086 3/2013
WO 2013040086 A1 3/2013

OTHER PUBLICATIONS

English translation of JP 3581319 B2 (Year: 2004).*
(Continued)

*Primary Examiner* — Huy Q Phan
*Assistant Examiner* — Haidong Zhang
(74) *Attorney, Agent, or Firm* — Meunier Carlin & Curfman LLC

(57) ABSTRACT

Methods of assessing or obtaining an indication of the presence of a cognitive disorder by analysing microstructural changes in regions of the brain are provided. The invention particularly relates to methods of assessing or obtaining an indication of the presence of types of dementia, for example Alzheimer's disease, by analysing changes in minicolumns in regions or layers of the cortex of the brain or of the whole brain.

9 Claims, 15 Drawing Sheets

Related U.S. Application Data continuation of application No. 15/564,344, filed as application No. PCT/GB2016/050982 on Apr. 7, 2016, now Pat. No. 10,884,090.

(51) Int. Cl.
*A61B 5/055* (2006.01)
*G01R 33/56* (2006.01)

(56) References Cited

U.S. PATENT DOCUMENTS

| | | | | |
|---|---|---|---|---|
| 10,884,090 | B2 * | 1/2021 | Chance | A61B 5/4088 |
| 2002/0173713 | A1 | 11/2002 | Pfefferbaum et al. | |
| 2007/0081707 | A1 * | 4/2007 | Sirohey | G16Z 99/00 |
| | | | | 382/128 |
| 2009/0292478 | A1 | 11/2009 | Avinash et al. | |
| 2009/0292557 | A1 * | 11/2009 | Sirohey | G06Q 10/00 |
| | | | | 707/999.1 |
| 2010/0284595 | A1 * | 11/2010 | Mori | G06T 7/30 |
| | | | | 600/410 |
| 2011/0085722 | A1 * | 4/2011 | Feiweier | G01R 33/56518 |
| | | | | 324/309 |
| 2011/0199084 | A1 * | 8/2011 | Hasan | G01R 33/5608 |
| | | | | 324/309 |
| 2012/0286777 | A1 | 11/2012 | Frost et al. | |
| 2014/0303487 | A1 | 10/2014 | James et al. | |
| 2016/0061917 | A1 | 3/2016 | Chase et al. | |
| 2017/0261584 | A1 | 9/2017 | James et al. | |

OTHER PUBLICATIONS

International Search Report mailed on Jun. 28, 2016, issued in connection with International Application No. PCT/GB2016/050982 filed on Apr. 7, 2016, 7 pages.
El-Zehiry, N. et al., "Effect of Minicolumnar Disturbance on Dyslexic Brains: An MRI Study", IEEE, 2006, 1336-1339.
Peterson, D. et al., "Left-Hemispheric Microstructural Abnormalities in Children with High-Functioning Autism Spectrum Disorder", Autism Research, 2014, 8(1), 61-72.
Di Rosa, E. et al., "Reduced neuron density, enlarged minicolumn spacing and altered ageing effects in fusiform Cortex in schizophrenia", Psychiatry Research, 2009, 166(2-3), 102-115.
Chance, Steven A., et al., "Minicolumn Thinning in Temporal Lobe Association Cortex but not Primary Auditory cortex in Normal Human Ageing", Acta Neuropathol, 2006, vol. 111, pp. 459-464, doi:10.1007/s00401-005-0014-z.
Chance, Steven A., et al., "Microanatomical Correlates of Cognitive Ability and Decline: Normal Ageing, MCI, and I \zheimer's Disease", Cerebral Cortex, 2011, pp. 1-9, doi:10.1093/cercor/bhq264.
Kolasinski, James, et al., "A Combined Post-Mortem Magnetic Resonance Imaging and Quantitative Histological Study of Multiple Sclerosis Pathology", Brain, 2012, vol. 135, pp. 2938-2951, doi:10.1093/brain/aws242.
Miller, Karla L., et al., "Diffusion Imaging of Whole, Post-Mortem Human Brains on a Clinical MRI Scanner", NeuroImage, 2011, vol. 57, pp. 167-181.
Van Veluw, Susanne J., et al., "Prefrontal Cortex Cytoarchitecture in Normal Aging and Alzheimer's Disease: A Relationship With IQ", Brain Struct Fune!, 2012, vol. 217(4), pp. 797-808, doi:10.1007/s00429-012-0381-x.
A Translational Tool for Characterising Fine Anatomical Structures, Osteotronix Lid, The Life Sciences Hub 3 | \ssembly Square, Cardiff CF 10 4PL, UK, [Retrieved from the Internet:URL:http://www.acuitasmedical.com/ echnology.php[retrieved on Nov. 16, 2017] an Abstract].
Buldyrev, et al., "Description of Microcolumnar Ensembles in Association Cortex and their Disruption in Alzheimer nd Lewy Body Dementias", Proc. Nall. Acad. Sci. USA, May 2000, vol. 97(10), pp. 5039-5043.

Chance, S.A., et al., "Minicolumnar Structure in Heschl's Gyrus and Planum Temporale: Asymmetries in Relation to Sex and Callosal Fiber Number", Neuroscience, 2006, vol. 143(4), pp. 1041-1050.
Chance, S.A., "Subtle Changes in the Ageing Human Brain", Nutrition and Health, 2006, vol. 18, pp. 217-224.
Chance, S.A., et al., "Auditory Cortex Asymmetry, Altered Minicolumn Spacing and Absence of Ageing Effects in Schizophrenia", Brain, 2008, vol. 131(12), pp. 3178-3192, doi:10.1093/brain/awn211.
Esiri, M.M., et al., "Vulnerability to Alzheimers Pathology in Neocortex: The Roles of Plasticity and Columnar Organization", Journal of Alz. Dis, 2006, vol. 9, pp. 79-89.
Esiri, M.M., et al., "Cognitive Reserve, Cortical Plasticity and Resistance to Alzheimers Disease", Alzheimers Research & Therapy, 2012, vol. 4(2), p. 7, doi:10.1186/alzrt105.
McKinstry, R.C., et al., "Radial Organization of Developing Preterm Human Cerebral Cortex Revealed by Non-nvasive Water Diffusion Anisotropy MRI", Cerebral Cortex, Dec. 1, 2002, vol. 12(12), pp. 1237-1243, hllps://doi.Jrg/10.1093/cercor/12.12.1237.
McNab, J.A., et al., High Resolution Diffusion-Weighted Imaging in Fixed Human Brain Using Diffusion-Weighted Steady State Free Precession, NeuroImage, 2009, vol. 46, pp. 775-785.
Casanova, M.F., "Neuropathological and Genetic Findings in Autism: The Significance of a Putative Minicolumnopathy", Neuroscientist, 2006, vol. 12(5), pp. 435-441, doi:10.1177/1073858406290375.
McKavanagh, R., et al., "DTI in the Cerebal Cortex Correlates with Axon Bundle Organisation: Investigation of Regional Differences in Autism", 2013 International Meeting for Autism Research: DTI in the Cerebal Cortex, May 2, J013. {Abstract only).
European Office Action, from the European Patent Office, for EP Application No. 16716652.9, dated Apr. 2, 2019, pp. 1-6.
Di Rosa, E., et al., "Axon Bundle Spacing in Anterior Cingulate Cortex in the Human Brain", Journal of Clinical Neuroscience, 2008, vol. 15(12), pp. 1389-1392.
Gabbott, P.L., et al., Visual Deprivation Alters Dendritic Bundle Architecture in Layer 4 of Rat Visual Cortex, Neuroscience, Apr. 5, 2012, vol. 207, pp. 65-77 {Abstract only).
Ringman, J.M., et al., "Diffusion Tensor Imaging in Preclinical and Presymptomatic Carriers of Familial Alzheimer's Disease Mutations", Brain, Aug. 2007, pp. 1-10.
Notice of Reasons for Refusal {machine translation), for Japanese Patent Application No. JP2018-503831, Feb. 17, 2020, pp. 1-11.
Buxhoeveden, D.P., et al., "Quantitative Analysis of Cell cols. in the Cerebral Cortex", Journal of Neuroscience Methods, 2000, vol. 97, pp. 7-17.
Casanova, M.F. and Switala, A.E., "Minicolumnar Morphometry: Computerized Image Analysis", in "Neocortical Modularity and the Cell Minicolumn", Manuel F. Cassanova, Editor, 2005, Nova Science Publishers, Inc., Chapter IX, p. 161-179.
Chance, S.A., et al., "The Cytoarchitecture of Sulcal Folding in Heschl's Sulcus and the Temporal Cortex in the Normal Brain and Schizophrenia: Lamina Thickness and Cell Density", Neuroscience Letters, 2004, vol. 367, pp. 384-388.
McDonald, B., et al., "Anomalous Asymmetry of Fusiform and Parahippocampal Gyrus Gray Matter in Schizophrenia: A Postmortem Study", Am. J_ Psychiatry, Jan. 2000, vol. 157(1), pp. 40-47.
McGurn, B., et al., "Pronunciation of Irregular Words is Preserved in Dementia, Validating Premorbid IQ Estimation", Neurology, 2004, vol. 62, pp. 1184-1186.
Peters, A., "The Morphology of Minicolumns", in "The Neurochemical Basis of Autism", Department of Anatomy and Neurobiology, Boston, MA, G.J. Blatt, Editor, 2010, pp. 45-68.
Summons to attend oral proceedings pursuant to Rule 115(1) EPC for European Application No. 16716652.9 dated Sep. 2, 2024.
El-Zehiry N and, Effect of Minicolumnar Disturbance on Dyslexic Brains: an MRI Study, Biomedical Imaging: Macro To Nano, Apr. 6, 2006, XP010912801.
Daniel Peterson et al., Left-Hemispheric Microstructural Abnormalities in Children With High Functioning Autism Spectrum Disorder, Autism Research, vol. 8.No. 1, Sep. 25, 2014, XP055281681.
Di Rosa E et al, Reduced neuron density, enlarged minicolumn spacing and altered ageing effects in fusiform cortex in schizophrenia, Psychiatry Research, Apr. 30, 2009. XP026029686.

(56) References Cited

OTHER PUBLICATIONS

Whitwell, J L et al, "Differentiation of bvFTD and Alzheimer's disease using grey matter DTI and volume measurements", Alzheimer's & Dementia, Elsevier, New York, NY, US, vol. 6, No. 4, Jul. 1, 2010, pp. S424-S425, XP027126947.

Mckavanagh R et al, "DTI in the Cerebral Cortex Correlates with Axon Bundle Organisation: Investigation of Regional Differences in Autism", May 2, 2013, XP093193918.

* cited by examiner

FROM FIG 11

- ◦ - CONTROL
- □ - AD

METHOD OF OBTAINING AN INDICATION OF AN EFFICACY OF A DRUG

CROSS-REFERENCE

This application is a continuation of U.S. patent application Ser. No. 17/115,129, filed Dec. 8, 2020, which is a continuation of U.S. patent application Ser. No. 15/564,344, filed Oct. 4, 2017, which is a U.S. national phase application under 35 U.S.C. § 371 of international application PCT/GB2016/050982, filed Apr. 7, 2016, which claims priority to Great Britain application 1505940.5, filed Apr. 8, 2015, all which are incorporated by reference in their entirety herein.

FIELD OF INVENTION

The present invention relates to methods of assessing or obtaining an indication of the presence of a cognitive disorder by analysing microstructural changes in regions of the brain. The invention particularly relates to methods of assessing or obtaining an indication of the presence of types of dementia, for example Alzheimer's disease, by analysing changes in minicolumns in regions of the cortex of the brain.

BACKGROUND OF THE INVENTION

Diagnosis and treatment of dementia is an increasing problem given the ageing population. Currently dementia affects over 830,000 people in the UK. However, given the difficulties in accurate diagnosis of these disorders, the actual proportion of people affected by these disorders may be much greater.

There are many recognised forms of dementia. These include Alzheimer's disease (AD), cerebrovascular disease (CVD), frontotemporal dementia (FTD) and dementia with Lewy Bodies (DLB). Mild Cognitive Impairment (MCI) is considered to be a precursor to dementia.

Current methods of diagnosis usually depend on clinical screening tools in the form of cognitive tests and assessment of behavioural symptoms. Currently, a standard structural brain MRI may often be requested in order to seek evidence of a qualitative (i.e. visually apparent) reduction in hippocampal volume, enlargement of ventricles and the appearance of enlarged sulcal folding of the cerebral cortex. This assessment is subjective and non-specific, and therefore whilst it provides additional evidence, it is not diagnostic in itself. Differential diagnosis of AD from CVD is usually dependent on the clinical assessment of disease course, with progressive cognitive decline being gradual in the case of AD in contrast to 'stepwise' (rapid drops interrupted by 'plateaus' of relative stability). Clearly this is also subjective and open to interpretation.

The current cognitive test is usually the MMSE (mini-mental state exam) for which 'healthy' is often considered to be a score >24, MCI 21-24 and dementia 20 or less. However, these boundaries are changeable and also open to interpretation. Some consider a score of <30 to be compatible with MCI. An additional test, the MoCA (Montreal cognitive assessment) has recently been found to be sensitive to CVD-type cognitive changes that may be missed by MMSE. However, it does not provide a differential diagnosis.

Currently, Alzheimer's disease and other forms of dementia can only definitively be diagnosed by post-mortem histology. The exact biochemical processes are not sufficiently understood to offer methods that are an accurate alternative to post-mortem examination. Additionally, most existing measurements of neuropathology in dementia depend on assessment of plaques, tangles or individual cells and synapses, which are at the microscopic level and thus cannot be detected using conventional non-invasive brain imaging.

Early diagnosis of these conditions is particularly important for effective clinical intervention to halt or slow the progression of the disease, since the neuropathological changes that occur in dementia are thought to start occurring significantly earlier than the appearance of symptoms.

An additional problem in this field of medicine is that, despite some shared risk factors, the clinical course and potential treatment strategies differ between different types of dementia, for example AD and CVD. Cognitive testing gives an indicator of decline in mental function, but with currently available tools it is difficult to discriminate between different types of dementia. Therefore, it is particularly important from a clinical perspective to be able to differentiate between different types of dementia so that the appropriate course of action and treatment can be taken.

Currently biomarker detection depends on: i) invasive methods for CSF or blood (which carry risk to patients); ii) invasive methods for imaging molecular markers in the brain (which carry risk to patients such that they cannot often be repeated); or iii) non-invasive brain imaging methods which are based on statistical number-crunching of population samples using standard volumetric MRI or more recent texture analysis of structural MRI (such as T1 or T2, for example).

The invention addresses this need for a non-invasive and accurate way of assessing the presence and/or severity of cognitive disorders including dementia, by assessing microstructural changes in the cortex.

SUMMARY OF THE INVENTION

The minicolumn microcircuit is considered to be the fundamental unit in the organisation and function of the cortex of the brain. Whilst it has been reported that minicolumn spacing of cells in human association cortex is reduced in normal aging (i.e. minicolumn thinning) (Chance S. A.; Casanova M. F.; Switala A. E.; Crow T. J.; Esiri M. M. Minicolumn thinning in temporal lobe association cortex but not primary auditory cortex in normal human ageing. *Acta Neuropathologica* 111(5):459-64 (2006)), few micro-anatomical measures have been reliably correlated with cognitive measures in ageing and Alzheimer's disease (AD), particularly in the early stages of degeneration, such as MCI. Recently, Chance et al. (Chance S. A.; Clover L.; Cousijn H.; Currah L.; Pettingill R.; Esiri M. M. Micro-anatomical correlates of cognitive ability and decline: normal ageing, MCI and Alzheimer's disease. *Cerebral Cortex* 21(8): 1870-8 (2011)) reported that minicolumn changes in two areas of the cortex (the association cortex in the planum temporale (BA22) and primary auditory cortex (BA41)) were correlated with pre-mortem cognitive scores (mini-mental state examination and verbal fluency) in both MCI and AD brains. However, whereas the association cortex showed a strong correlation with cognitive function, in the primary auditory cortex this relationship was an epiphenomenon of overall brain atrophy. Therefore it remains unknown whether there are specific patterns of changes in the brains of patients with cognitive disorders such as dementia. In particular, whether distinct patterns of change occur in different types of dementia remains unknown.

The inventors have found that signature patterns of micro-anatomical changes within certain regions of the brain associated with neuropathological conditions do indeed exist and correlate with cognitive ability and decline. These signature patterns can be used as biomarkers or predictors of the presence and also severity/staging of cognitive disorders in a living subject, as described in the present invention. A distinct advantage of the present invention is that the characteristic patterns of brain 'signatures' described herein are detectable in life, and with existing non-invasive techniques which are far safer than other potential methods of detection currently based on invasive methods.

These patterns of microstructural changes occur in specific regions of the brain and the pattern of changes observed in different regions of the brain is specific to particular cognitive disorders. These patterns can therefore be used as a biomarker to assess the likelihood of whether a subject has a particular cognitive disorder, and if the presence of such a disorder is indicated, the methods of the invention can also be used to assess the severity of the cognitive disorder.

Given that these signature patterns are specific to particular cognitive disorders, these methods may also be used for discriminating between different types of cognitive disorders which can be difficult to distinguish using currently available diagnostic tools.

These signature patterns can be quantified non-invasively using data derived from MRI scanning and imaging methods applied to the brains of subjects, using different MRI methods including but not limited to diffusion tensor imaging (DTI), Fine Structure Analysis (fineSA™, see: http://www.acuitasmedcal.com/technology.php) and other MRI acquisition methods. The data derived from these imaging studies can then be compared to the predicted pattern of change determined from patients with confirmed diagnoses of such conditions. This comparison of acquired data from a subject of interest with the modelled data derived from patients with confirmed diagnoses will then aid in the assessment and diagnosis of different types of dementia or other cognitive disorders in living subjects, including early stages of dementia.

The inventors have also found that diffusion MRI measures, particularly DTI, can be used to assess minicolumn structure in the brain. Whilst DTI measures in the white matter have been conducted in other studies indicating changes in AD, these studies have only assessed the white matter of the brain. DTI is standard as an analysis of white matter in the brain, providing information regarding axonal fibre tracts, for example. In contrast, the analysis of DTI measures in the cortical grey matter is entirely different, with a different interpretation (since minicolumns do not exist in the white matter). Thus the invention also provides a new way of assessing minicolumn structure in the brain, which may be useful in the assessment of cognitive diseases in a clinical setting.

A further advantage of this invention is that the target, i.e. the minicolumn (including axon bundles and dendrites), is unique as a 'mesoscopic' structure that has a periodic, directional structure at a scale that can be detected as a signal using new, high resolution imaging methods (such as DTI, Fine Structure Analysis or other MRI acquisition methods), in contrast to existing microscopic measurements of neuropathology in dementia which depend on assessment of plaques, tangles or individual cells and synapses at the microscopic level which cannot be observed using conventional non-invasive brain imaging.

The invention may be particularly useful in providing a method for diagnosing or staging Alzheimer's disease and other dementias using signature patterns of microstructural brain changes.

The invention may also be applied to other cognitive disorders or neurological conditions where there are structural changes in the brain. Such cognitive disorders include autism, schizophrenia, bipolar disorder, epilepsy, dyslexia, Down's syndrome, Parkinson's disease, amyotrophic lateral sclerosis, Huntington's disease, multiple sclerosis, prion disease, depression, obsessive-compulsive disorder, and attention deficit hyperactivity disorder (ADHD).

DETAILED DESCRIPTION OF THE INVENTION

Figure 1:
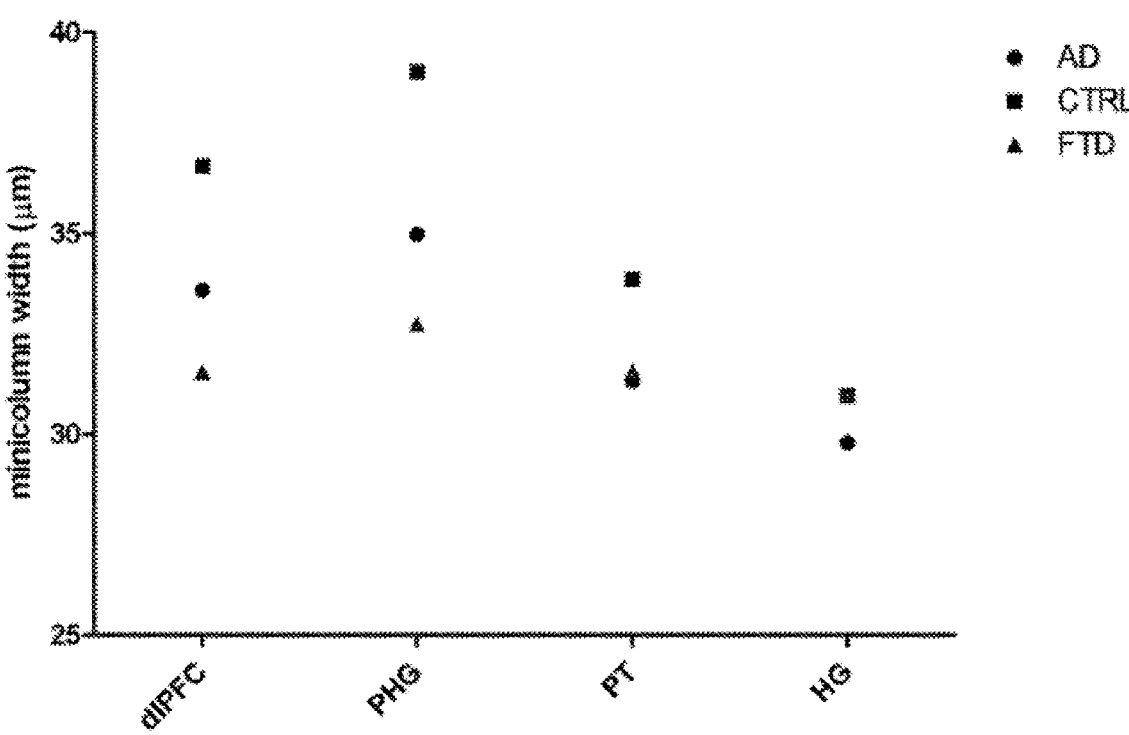
FIG. 1 shows minicolumn width (μm) in different areas for controls (CTRL), AD, and FTD patients. Both in the dIPFC and PHG the CTRL group is significantly different from the AD and FTD group. In the PT, the CTRL group is significantly different from the AD group.
Figure 2:
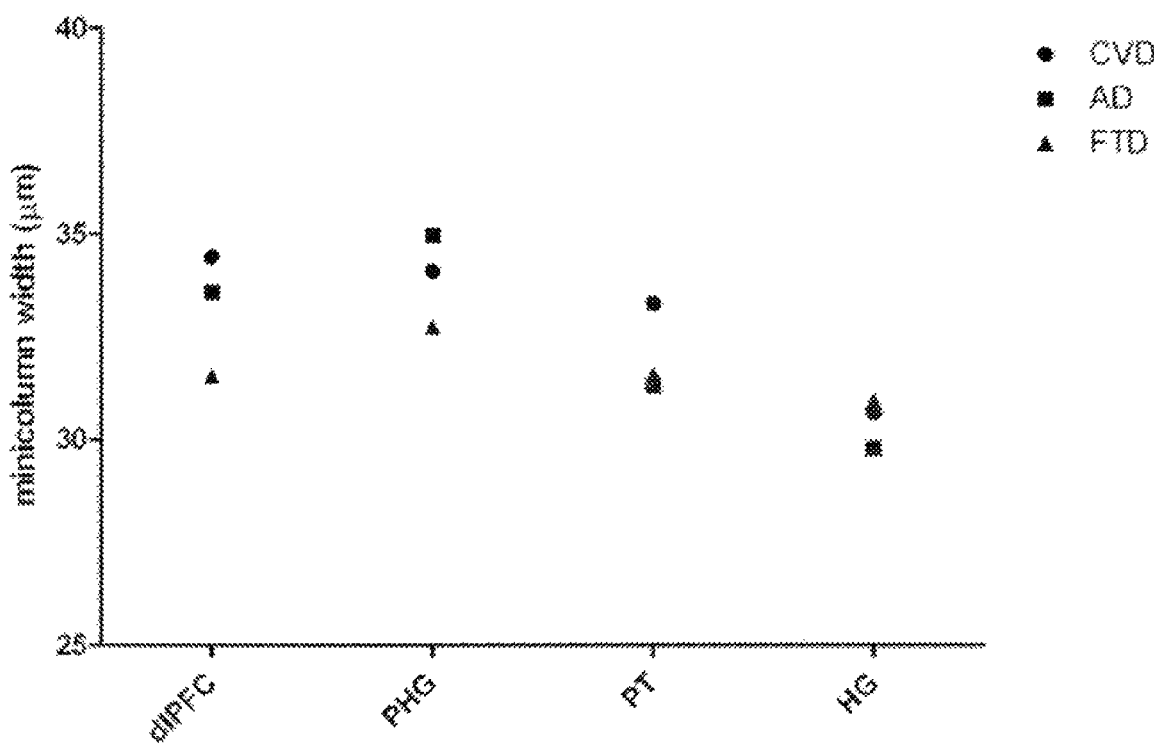
FIG. 2 shows minicolumn width (μm) in different areas for CVD, AD, and FTD patients. CVD is only significantly different from FTD in the dIPFC.
Figure 3:
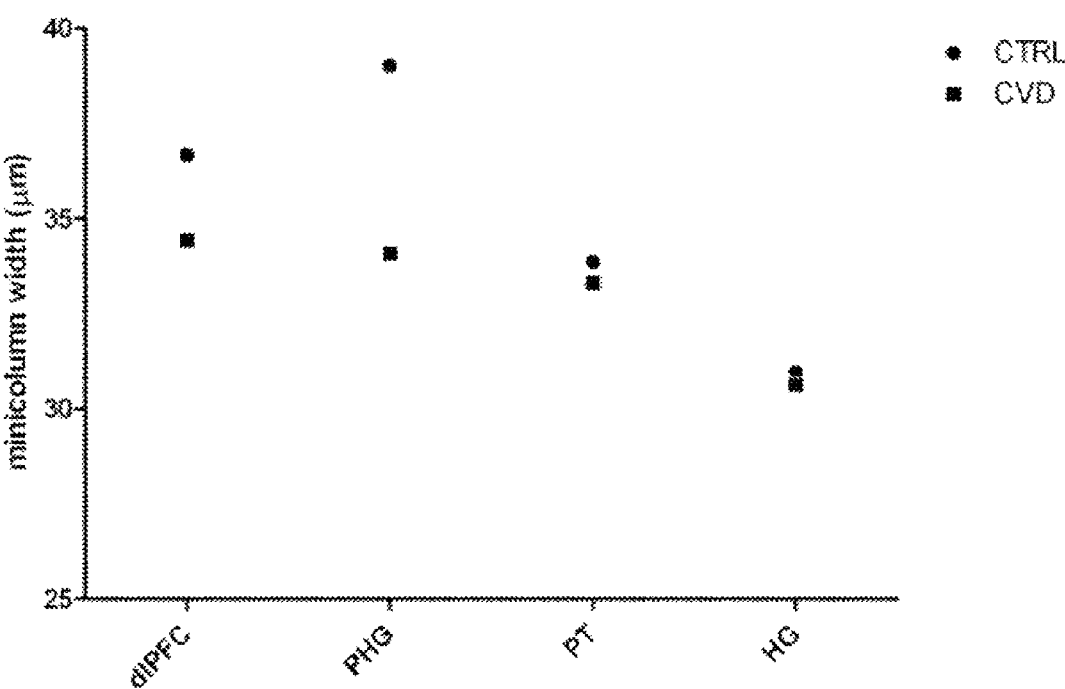
FIG. 3 shows minicolumn width (μm) in different areas for CTRL's and the CVD group. The CTRL group is significantly different than the CVD group for both dIPFC and PHG.
Figure 4:
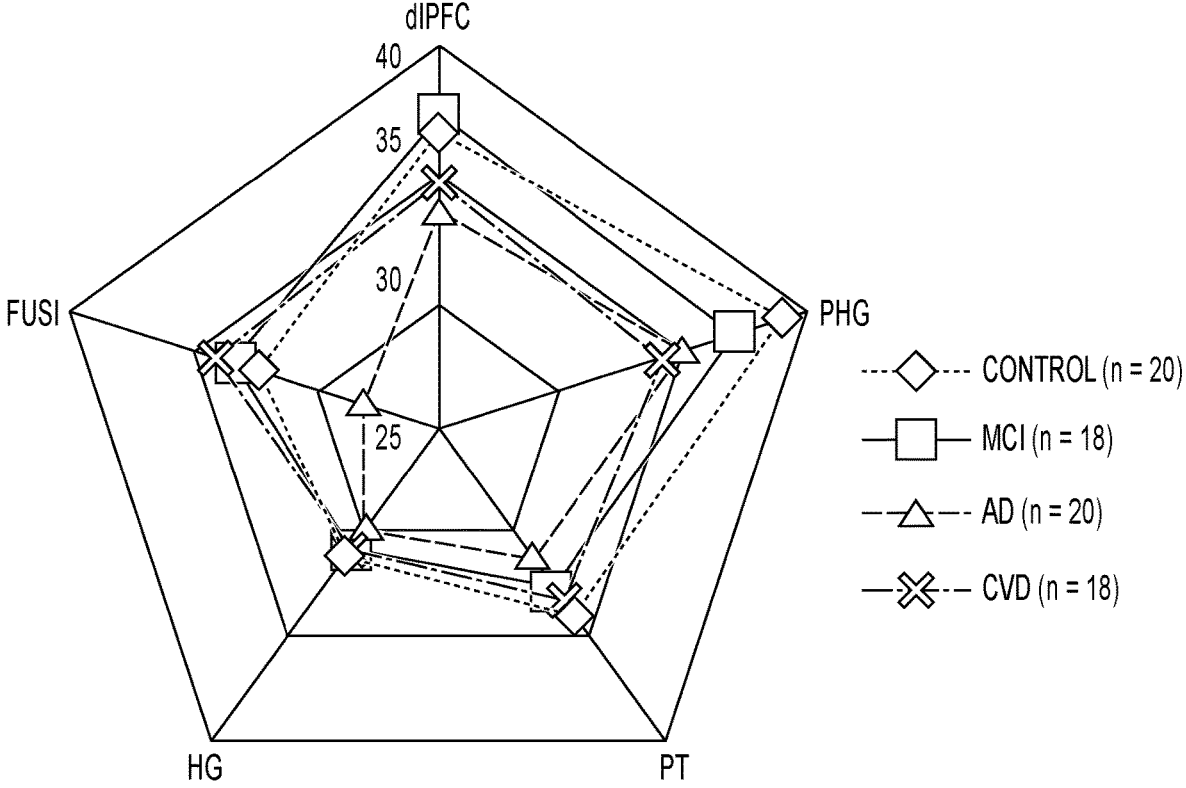
FIG. 4 shows minicolumn width (μm) in different areas (dIPFC, PHG, PT, HG and Fusi) for CTRL's, MCI, AD and CVD groups.
Figure 5:
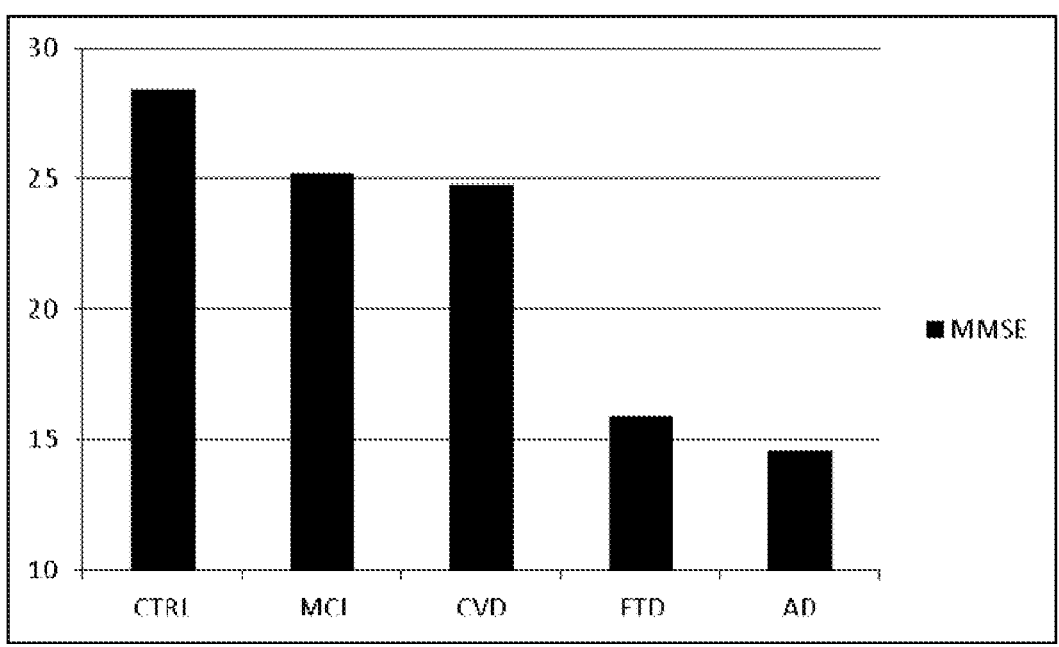
FIG. 5 shows MMSE score for different groups.
Figure 6:
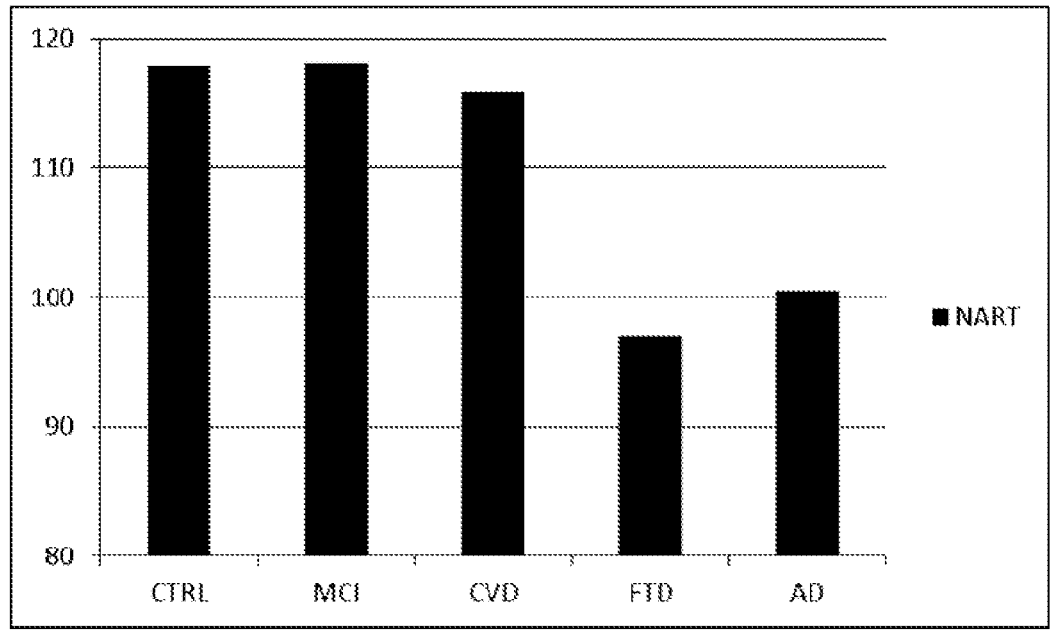
FIG. 6 shows NART score for different groups.

It is therefore an object of the invention to provide a method of assessing or obtaining an indication of the presence of a cognitive disorder in a subject by analysing microstructural changes in regions of the brain.

It is another object of the invention to provide a method of assessing or obtaining an indication of the presence of types of dementia, for example Alzheimer's disease, by analysing microstructural changes in regions of the cortex of the brain.

In one embodiment, the invention provides a method of obtaining an indication of the presence of a cognitive disorder in a subject, the method comprising the steps of correlating:

(a) one or more diffusion MRI measurements of minicolumn-based parameters obtained from the subject's brain, or values derived therefrom; and (b) the presence or absence of a cognitive disorder in the subject, thereby obtaining an indication of the presence of a cognitive disorder in the subject.

The invention also provides a method of obtaining an indication of the presence of a cognitive disorder in a subject, the method comprising the step of: (a) determining from one or more diffusion MRI measurements of minicolumn-based parameters obtained from the subject's brain, or values derived therefrom, an indication of the presence of a cognitive disorder in the subject.

Preferably, the determining step comprises comparing the diffusion MRI measurement(s) of the minicolumn-based parameter(s) obtained from the subject's brain, or values derived therefrom, with corresponding diffusion MRI measurements or values derived therefrom obtained from one or more control subjects with defined cognitive disorders, thereby obtaining an indication of the presence of a cognitive disorder in the subject.

The invention also provides a method of obtaining an indication of the presence of a cognitive disorder in a subject, the method comprising the steps of comparing:

(a) one or more diffusion MRI measurements of minicolumn-based parameters obtained from the subject's brain, or a value derived therefrom; and (b) the corresponding measurement(s) or value(s) obtained from a control subject without a cognitive disorder, wherein if the measurement or value obtained in step (a) is one which is positively correlated or directly proportional to the likelihood of the subject having a cognitive disorder, an increase in the measurement or value obtained in step (a) compared to the corresponding measurement or value in step (b) is indicative of the subject having a cognitive disorder; and wherein if the measurement or value obtained in step (a) is one which is negatively correlated or inversely proportional to the likelihood of the subject having a cognitive disorder, a decrease in the measurement or value obtained in step (a) compared to the corresponding measurement or value in step (b) is indicative of the subject not having a cognitive disorder.

The invention also provides a method of obtaining an indication of the prognosis of a subject with a cognitive disorder, the method comprising the steps of comparing:

(a) one or more diffusion MRI measurements of minicolumn-based parameters obtained from the subject's brain, or values derived therefrom, with (b) corresponding previously-obtained diffusion MRI measurements obtained from the subject's brain, or corresponding values derived therefrom, wherein a change in the measurement or value obtained in step (a) compared to the corresponding measurement or value obtained in step (b) is indicative of a change in the prognosis for the subject.

If the measurement or value obtained in step (a) is one which is positively correlated or directly proportional to the severity of the cognitive disorder, an increase in the measurement or value obtained in step (a) compared to the corresponding measurement or value in step (b) is indicative of a decline in the prognosis for the subject, and a decrease in the measurement or value obtained in step (a) compared to the corresponding measurement or value in step (b) is indicative of an improvement in the prognosis for the subject.

If the measurement or value obtained in step (a) is one which is negatively correlated or inversely proportional to the severity of the cognitive disorder, a decrease in the measurement or value obtained in step (a) compared to the corresponding measurement or value in step (b) is indicative of a decline in the prognosis for the subject, and an increase in the measurement or value obtained in step (a) compared to the corresponding measurement or value in step (b) is indicative of an improvement in the prognosis for the subject.

The invention also provides a method of obtaining an indication of the efficacy of a drug which is being used to treat a cognitive disorder in a subject, the method comprising the steps of:

(a) comparing first and second diffusion MRI measurements of minicolumn-based parameters obtained from the subject's brain, or values derived therefrom, wherein the drug has been administered to the subject in the interval between the taking of the first and second MRI measurements, wherein if the measurement or value obtained in step (a) is one which is positively correlated or proportional to the severity of the cognitive disorder, an increase in the second measurement or value obtained in step (a) compared to the first measurement or value is indicative of the lack of efficacy of the drug; and a decrease in the second measurement or value obtained in step (a) compared to the first measurement or value is indicative of the efficacy of the drug.

If the measurement or value obtained in step (a) is one which is negatively correlated or inversely proportional to the severity of the cognitive disorder, an increase in the second measurement or value obtained in step (a) compared to the first measurement or value is indicative of the efficacy of the drug; and a decrease in the second measurement or value obtained in step (a) compared to the first measurement or value is indicative of the lack of efficacy of the drug.

In yet another embodiment, the invention provides a method of obtaining an indication of the presence of a specific cognitive disorder in a subject, the method comprising the steps of correlating:

(a) one or more minicolumn-based parameters or values derived therefrom from one or more regions of the brain of the subject, with (b) the presence of a specific cognitive disorder in a subject, thereby obtaining an indication of the presence of a specific cognitive disorder in the subject.

The invention also provides a method of obtaining an indication of the presence of a specific cognitive disorder in a subject, the method comprising the step:

(a) determining from one or more minicolumn-based parameters or values derived therefrom from one or more regions of the brain of the subject an indication of the presence of a specific cognitive disorder in the subject.

Preferably, the determining step comprises comparing the one or more minicolumn-based parameters or values derived therefrom from one or more regions of the brain of the subject with corresponding minicolumn-based parameters or values derived therefrom from one or more regions of the brains of one or more control subjects with defined cognitive disorders, thereby obtaining an indication of the presence of a specific cognitive disorder in the subject.

The invention also provides a method of obtaining an indication of the presence of a specific cognitive disorder in a subject, the method comprising the steps of:

(i) comparing one or more minicolumn-based parameters or values derived therefrom from one or more regions of the brain of the subject, with (ii) a reference set of minicolumn-based parameters or values derived therefrom from corresponding regions of the brains of control subjects with specific cognitive disorders, thereby obtaining an indication of the presence of a specific cognitive disorder in the subject.

The invention further provides a method of obtaining an indication of the presence of a specific cognitive disorder in a subject, the method comprising the steps of comparing:

(i) a signature pattern obtained from one more minicolumn-based parameters or values derived therefrom from one or more regions of the brain of the subject, with (ii) a reference signature pattern obtained from minicolumn-based parameters or values derived therefrom from one or more regions of the brains of control subjects with specific cognitive disorders, thereby obtaining an indication of the presence of a specific cognitive disorder in the subject.

The invention also provides a computer-implemented method of obtaining a measurement of a minicolumn-based parameter in a region of the brain of a subject, the method comprising the steps of:

(a) comparing one or more diffusion MRI measurements obtained from a region of the brain of the subject or values derived therefrom, with (b) a reference set of diffusion MRI measurements or values derived therefrom from corresponding regions of the brains of control subjects with defined minicolumn-based parameters, thereby obtaining a measurement of the minicolumn-based parameter in the region of the brain of the subject.

The invention also provides a computer-implemented method of deriving a signature pattern from one or more minicolumn-based parameters in a region of the brain of a subject, the method comprising the steps of:

(a) comparing one or more diffusion MRI measurements obtained from a region of the brain of the subject, or values derived therefrom, with a reference set of diffusion MRI measurements or values derived therefrom from corresponding regions of brains of control subjects with defined minicolumn-based parameters, thereby obtaining measurements of one or more minicolumn-based parameters in the region of the brain of the subject, and (b) deriving a signature pattern from the measurements of the one or more minicolumn-based parameters in the region of the brain of the subject.

In a particularly preferred embodiment of the methods of the invention, the one or more minicolumn-based parameters are obtained by diffusion MRI.

As used herein, the term "cognitive disorder" refers to any mental health disorder that affects learning, memory, perception, and/or problem solving.

In preferred embodiments of the invention, the cognitive disorder may be any form of dementia.

Preferably, the cognitive disorder is selected from the group consisting of (i) Alzheimer's Disease (AD), (ii) cerebrovascular dementia (CVD), (iii) mild cognitive impairment (MCI), (iv) frontotemporal dementia (FTD), and (v) dementia with Lewy Bodies (DLB).

In other embodiments, the cognitive disorder may be a neurological disorder associated with changes in normal brain structure, preferably a neurological disorder selected from the group consisting of (i) autism, (ii) multiple sclerosis (MS), (iii) epilepsy, (iv) amyotrophic lateral sclerosis (ALS) and (v) Parkinson's disease.

In other embodiments, the cognitive disorder is preferably a neuro-psychiatric disorder, most preferably selected from the group consisting of schizophrenia, bipolar disorder, dyslexia, Down's syndrome, Huntington's disease, prion disease, depression, obsessive-compulsive disorder and attention deficit hyperactivity disorder (ADHD). In some preferred embodiments, the cognitive disorder is an autism spectrum disorder.

As used herein, the term "diffusion MRI" refers to any magnetic resonance imaging (MRI) method which measures the diffusion process of molecules, preferably water molecules, in biological tissues. Diffusion MRI may also be referred to as diffusion tensor imaging (DTI).

Preferably, the diffusion MRI measurement is selected from perpendicular diffusivity, mean minicolumn diffusivity, radial diffusivity, minicolumn width, mean diffusivity, fractional anisotropy, grey matter density and angle of columnar deviation, or a value derived therefrom.

Perpendicular diffusivity is the component of the diffusion occurring in the principle diffusion direction that is perpendicular to the radial direction across the cortex. This can be measured by multiplying the main eigenvector (V1) by the value of its corresponding eigenvalue (L1), then resolving this into its components. The value of the component perpendicular to the radial direction across the cortex is the perpendicular diffusivity.

Minicolumn diffusivity is the combination of the components of diffusion across multiple diffusion directions that are perpendicular to the radial direction across the cortex. This can be measured by taking the eigenvalues from all three eigenvectors and combining the components of the eigenvalues that are perpendicular to the radial direction across the cortex in order to create a mean value.

Mean diffusivity is a measure of the total diffusion occurring in a voxel. It is calculated by finding an average of the three eigenvalues (i.e. $(L1+L2+L3)/3$). For the analysis presented herein, the value of each of these is calculated for each voxel individually. A weighted average of the values along each cortical profile is then calculated to give the mean diffusivity.

Radial diffusivity is the component of the diffusion occurring in the principle diffusion direction that is parallel to the radial direction across the cortex. This can be measured by multiplying the main eigenvector (V1) by the value of its corresponding eigenvalue (L1), then resolving this into its components. The value of the component parallel to the radial direction across the cortex is the radial diffusion. For the avoidance of any doubt, it should be noted that the term "radial diffusion" has also become a term which is often applied to white matter, referring to the amount of diffusion perpendicular to the primary diffusion direction (a definition which is dependent on the intrinsic diffusion signal in any voxel). However, that is not the same as the measurement as used herein, which specifically refers to the anatomical radial direction across the cerebral cortex (a definition which is related to anatomy, specifically the expected radial direction of minicolumns).

Fractional anisotropy (FA) is a measure of the degree of anisotropy, or directional dependence, of a process, where zero represents isotropic or unrestricted diffusion, and 1 represents diffusion occurring along only one axis with total restriction along the other axes.

As used herein, the term "angle of columnar deviation" is used interchangeably with the terms angle of deviation, V1_angle and V1_angle of deviation. It is defined as the difference between the estimated columnar direction which is the radial direction across the cortex, and the direction of the main eigenvector (V1), expressed as an angle. The angles of the other eigenvectors (V2, V3) relative to the estimated radial direction across the cortex may also be used.

Individual structural MRI scans can be registered to a group average template and then segmented into white and grey matter density before being smoothed. This results in images where each voxel contains an average grey matter density calculated over the surrounding voxels.

Diffusion MRI measurements are correlated with minicolumn width and minicolumn spacing. Particular types of diffusion MRI measurements, or values derived therefrom, may be directly proportional (positively correlated) or inversely proportional (negatively correlated) to minicolumn width and minicolumn spacing.

Perpendicular diffusion and mean diffusivity are each inversely proportional to minicolumn width and minicolumn spacing. Minicolumn width and minicolumn spacing are correlated within subjects with cognitive disorders. Therefore, perpendicular diffusion and mean diffusivity are increased in subjects with cognitive disorders such as AD when compared to normal control subjects without said cognitive disorder. Perpendicular diffusion and mean diffusivity also increase as the severity of the cognitive disorder increases.

In contrast, radial diffusivity, fractional anisotropy and grey matter density are each proportional to minicolumn width and minicolumn spacing. Minicolumn width and minicolumn spacing are correlated with cognitive disorders. Therefore, radial diffusivity, fractional anisotropy and grey matter density are decreased in subjects with cognitive disorders such as AD when compared to normal control subjects without said cognitive disorder. Radial diffusivity, fractional anisotropy and grey matter density also decrease as the severity of the cognitive disorder increases.

In embodiments wherein the diffusion MRI measurement or a value derived therefrom is previously-obtained or derived from a control subject, the measurement or value derived therefrom may be obtained from a graph, look-up table, database or mathematical equation, or the like.

Examples of diffusion MRI measurements which are positively correlated with or are directly proportional to the likelihood of the subject having a cognitive disorder or the severity of the cognitive disorder include: perpendicular diffusivity, and mean minicolumn diffusivity.

Examples of diffusion MRI measurements which are negatively correlated with or are inversely proportional to the likelihood of the subject having a cognitive disorder or the severity of the cognitive disorder include: radial diffusivity, fractional anisotropy and grey matter density.

As used herein, the term "signature pattern" refers to a pattern, profile or fingerprint of one or more minicolumn-based parameters which is characteristic of a specific cognitive disorder. This signature pattern can be used to help to distinguish between specific cognitive disorders. In its simplest form, the signature pattern may be a single parameter, e.g. minicolumn width or minicolumn spacing.

In other embodiments, the signature pattern may be a mathematical formula or equation or multi-parameter function which incorporates one or more minicolumn-based parameters and optionally one or more non-minicolumn-based parameters. The formula or equation or function may be linear or non-linear, and may include squares or higher powers of the parameters.

Non-minicolumn-based parameters may include levels of specific proteins in the brain or in certain brain regions, or parameters based on defined physiological structures, e.g. plaque levels or protein tangles.

Other non-minicolumn-based parameters include those defined herein at MRI diffusion measurements or values derived therefrom.

In some embodiments, the invention provides a method of obtaining an indication of the presence or absence of a specific cognitive disorder in a subject, the method comprising the step of comparing:

(i) one or more minicolumn-based parameters or values derived therefrom from one or more regions of the brain of the subject, with (ii) one or more reference sets of minicolumn-based parameters or values derived therefrom from corresponding regions of the brains of control subjects, wherein the reference sets are obtained from control subjects with different specific cognitive disorders or without specific cognitive disorders, wherein if the minicolumn-based parameters or values derived therefrom obtained from the subject are within the range of the reference set of measurements or values derived therefrom from corresponding regions of the brains of control subjects with a specific cognitive disorder, then this provides an indication of the presence of that specific cognitive disorder in the subject; and wherein if the minicolumn-based parameters or values derived therefrom obtained from the subject are within the range of the reference set of measurements or values derived therefrom from corresponding regions of the brains of control subjects without a specific cognitive disorder, then this provides an indication of the absence of that specific cognitive disorder in the subject.

In some embodiments, a reduction in the minicolumn width in the prefrontal cortex and parahippocampal gyrus compared to non-diseased controls is indicative of the subject having CVD.

In other embodiments, a reduction in minicolumn width in all of the dlPFC (dorsolateral prefrontal cortex), PHG (parahippocampal gyrus), PT (planum temporale), HG (Heschl's gyrus—primary auditory region), and Fusi (Fusiform gyrus) compared to non-diseased controls is indicative of the subject having Alzheimer's Disease.

In embodiments of the invention, the minicolumn-based parameters obtained from the subjects' brains are obtained by a neuro-imaging method.

In preferred embodiments of the invention, the minicolumn-based parameters are measured using magnetic resonance imaging (MRI) of the brain.

The minicolumn-based parameters may be measured directly from an MRI scan of the subject's brain or from MRI data previously-obtained from the subject's brain.

In some embodiments, the MRI measurement may be a value that is derived from the individual brain MRI measurements using mathematical formulas, algorithms, databases and/or look-up tables.

In preferred embodiments, the value is derived from MRI measurements obtained from the brain or from images of the brain.

In some embodiments of the invention, the minicolumn measurements are obtained by diffusion MRI.

In other embodiments, the minicolumn-based parameters are obtained using T1 or T2 or T2* mapping or the MRI measurement may be a spectroscopic measurement of T1, T2, or T2* localised to the brain.

In some embodiments, the one or more measurements are preferably obtained using the imaging methods described in WO2013/040086 (the contents of which are hereby incorporated by reference) or Fine Structure Analysis™ (fineSA™; Acuitas Medical) or other MRI acquisition methods.

In some embodiments of the invention, the minicolumn-based parameters used as the control (to which the measurements obtained in the subject are compared) may be obtained histologically.

In other embodiments of the invention, the minicolumn-based parameters used as the control are obtained by the same method as the minicolumn-based parameters obtained from the subject.

As used herein, the term "minicolumn" is a vertical column through the cortical layers of the brain. Minicolumns may also be referred to interchangeably as cortical minicolumns, microcolumns or cortical microcolumns.

The term "minicolumn" may either be understood to be the combination of the cell-dense core and cell-sparse peripheral neuropil space surrounding it or, in some circumstances, just the cell-dense core (defined by the cell bodies). Typically, it relates to the core and periphery.

The minicolumn-based parameter may be a directly measurable feature of the minicolumn, preferably a microstructural or cytoarchitectural feature of the minicolumn.

Examples of directly measurable minicolumn-based parameters include minicolumn width, minicolumn spacing, axonal fibre bundle width, axonal fibre bundle spacing, dendritic fibre bundle width, dendritic fibre bundle spacing, minicolumn core width, and minicolumn peripheral neuropil space.

Preferably, the minicolumn-based parameter is minicolumn width or minicolumn spacing.

The minicolumn-based parameter may also be one which is an indirectly measured or a derived feature. Such features may be correlated with or proportional to a directly measurable feature of the minicolumn and therefore provide an indicator or biomarker of a directly measured feature of the minicolumn. Examples of indirectly measured or derived minicolumn-based parameters include perpendicular diffusion, mean diffusivity or radial diffusivity, fractional anisotropy or grey matter density, as defined above. As discussed previously, these parameters are correlated with or proportional to parameters such as minicolumn width, and so provide an indicator or biomarker of minicolumn width.

Minicolumn width is defined as the width of the minicolumn core (see below) and half of the peripheral neuropil space (see below) on either side of it. The mean minicolumn width may be used, preferably in conjunction with a defined brain region.

Minicolumn width may be measured histologically as follows. Images are typically acquired from a stained microscope section of the dissected cerebral cortex (typically using a standard Nissl stain such as Cresyl violet). The image is automatically segmented to select neurons and nearest-neighbour measurements of clustering are applied to determine the periodicity of columnar distribution. Segmentation is based on grey level intensity of the digitized photo-micrographic image, with automated shape and size thresholds for cell identification. Columnar organization is calculated using the Euclidean distance minimum spanning trees based on the cell centroids. These methods are described in Chance S. A.; Casanova M. F.; Switala A. E.; Crow T. J.; Esiri M. M. Minicolumn thinning in temporal lobe association cortex but not primary auditory cortex in normal human ageing. *Acta Neuropathologica* 111(5):459-64 (2006)] and [Chance S. A.; Clover L.; Cousijn H.; Currah L.; Pettingill R.; Esiri M. M. Micro-anatomical correlates of cognitive ability and decline: normal ageing, MCI and Alzheimer's disease. *Cerebral Cortex* 21(8):1870-8 (2011)].

Minicolumn spacing is defined as the centre-to-centre spacing of the minicolumns, and so includes both the cell bodies of the neurons and the neuropil space. When based on the average minicolumn core and average peripheral neuropil space across multiple minicolumns within a patch of cerebral cortex, the mean centre-to-centre spacing is effectively the same as the mean minicolumn width.

Minicolumn spacing may be measured histologically as follows. Images are typically acquired from a stained microscope section of the dissected cerebral cortex (typically using a standard Nissl stain such as Cresyl violet). The image is automatically segmented to select neurons and nearest neighbour measurements of clustering are applied to determine the periodicity of columnar distribution. Segmentation is based on grey level intensity of the digitized photo-micrographic image, with automated shape and size thresholds for cell identification. Columnar organization is calculated using the Euclidean distance minimum spanning trees based on the cell centroids.

Minicolumn core width is defined as the part of the column that contains 90% of the cell bodies. Minicolumn core width may be measured as follows. Having identified the neuronal cell bodies, a computer program is able to identify the vertical centre of the cell dense core based on the cell distribution and measure the width of the area containing 90% of the neuronal cell bodies.

Minicolumn peripheral neuropil space refers to the surrounding neuropil containing mostly neurite (mainly dendrites and axons) with very few cell bodies, which along with the minicolumn core, makes up the minicolumn. Minicolumn peripheral neuropil space can be calculated by subtracting the measure of the minicolumn core from the value of the minicolumn width.

Minicolumns consist of a vertical string of neurons, along with the associated axons and dendrites. Multiple individual axons group together, forming bundles as they descend from layers III to VI within, or closely adjacent to, the core of the minicolumn. Therefore, axon bundle spacings are thought to provide a similar measurement of the columnar organisation of the cortex to that provided by the measurement of minicolumn width.

Measurements of axonal bundle centre-to-centre spacing are made manually in image analysis software, using linear measurement tools. A sample line of standard length is drawn across the centre of a digital photo-micrograph, perpendicular to the bundle direction in order to identify the bundles to be measured. Only bundles intersecting this line are measured, those that pass out of the plane of sectioning above or below the line are not included. Single axons or pairs of axons crossing the line are not considered to constitute axon bundles for the purposes of this analysis. Bundles (>2axons) are identified and their centres marked (using a typical axon fibre or myelin stain such as sudan black or Palmgren's silver stain). Bundle spacing measurements are then made from the centre of each bundle marked in this way to the centre of the adjacent bundle, for all bundles intersecting this line.

A variant of the technique based on horizontal sections (similar to that described below for dendrite bundles) is given in Di Rosa E.; Crow T. J.; Chance S. A. Axon bundle spacing in anterior cingulate cortex in the human brain. *Journal of Clinical Neuroscience* 15(12):1389-1392 (2008). Axon bundle width refers to the width of the axon bundles associated with each minicolumn.

After identifying the axon bundles as described for the measurement of axon bundle spacing, the width of the axon bundles is made using standard linear measurement tools in any suitable image analysis software. The edges of the bundles are marked at the point where they intersect the horizontal line, and the bundle width is determined as the distance between these two points. Edges of axon bundles are distinguished by the change in intensity of staining from the background, which identifies the start of the more darkly stained axon bundle (using a typical axon fibre or myelin stain such as sudan black or Palmgren's silver stain).

Dendrite bundles are the bundles of dendrites that extend vertically (in the direction of the minicolumns) through the cerebral cortex. They are the dendritic equivalent of axon bundles.

They can be measured in a similar way to axon bundles though often they have been measured differently, using horizontal sections of cerebral cortex which transect the dendrites. Individual dendrites are therefore seen as individual points on stained sections and the bundle is measured as a 'cluster' of these points based on their distribution within the 2-dimensional section. The spacing of these bundles is then based on the 'inter-cluster distance'. This spacing may be either defined as the mean distance between the perimeters of neighbouring clusters or as the mean distance between the geometric centroids of the clusters. More details of such a technique are provided in Gabbott, P. L. and Stewart, M. G. (2012). Visual deprivation alters dendritic bundle architecture in layer 4 of rat visual cortex. Neuroscience, 207 pp. 65-77.

Dendrite bundle width is the width of the bundle of dendrites that extend vertically (in the direction of the minicolumns) through the cerebral cortex. This is the dendritic equivalent to axon bundle width and may be measured in a similar way to axon bundles, but has often been measured differently using horizontal sections (as described for dendrite bundle spacing, above). In this case, the dendrite 'cluster' has a mean diameter which will constitute the dendrite bundle width.

In preferred embodiments of the invention, the minicolumn-based parameter measurements are obtained from one or more different regions of the brain, preferably two or more, three or more, four or more, five or more, six or more, seven or more, or eight or more different regions of the brain, most preferably five or more different regions of the brain. The term "one or more regions of the brain" includes the whole brain.

In preferred embodiments of the invention, the minicolumn-based parameters are obtained from or derived from one or more regions or layers of the cortex of the brain.

In preferred embodiments, the minicolumn-based parameters are obtained from one or more specific layers of the cortex, preferably from cortical layer 3, cortical layer 5, or cortical layers 3-6.

In more preferred embodiments, the parameters are obtained from cortical layers 3-6 since these also contain axon bundles which may be useful for DTI signal analysis.

Preferably, the brain regions are selected from the group consisting of the parahippocampal gyrus (PHG), fusiform gyrus (Fusi), dorsolateral prefrontal cortex area 9 (dlPFC), Heschl's gyrus (HG), planum temporale (PT), inferior parietal lobule (IPL), middle temporal gyrus (MTG) and primary visual cortex (V1; area 17).

In some embodiments of the invention, the brain region is preferably the cortical grey matter.

In some preferred embodiments, the minicolumn-based parameters are obtained from or derived from 1, 2, 3, 4, 5, 6, 7 or 8 of the above regions.

In preferred embodiments of the invention where the method is used to distinguish between AD and CVD, the minicolumn-based parameters are obtained from or derived from one or more regions selected from the group consisting of the parahippocampal gyrus (PHG), fusiform gyrus (Fusi), dorsolateral prefrontal cortex area 9 (dlPFC), Heschl's gyrus (HG), and planum temporale (PT). In some preferred embodiments of the invention where the method is used to distinguish between AD and CVD, the minicolumn-based parameters are obtained from all of these regions. Use of parameters obtained from or derived from all five of these regions in the methods of the invention achieves >94% predictive accuracy for differentiating AD from CVD.

In preferred embodiments of the invention where the method is used to obtain an indication of the presence of Mild Cognitive Impairment (MCI), the minicolumn-based parameters are obtained from or derived from one or more regions of the cortex of the brain, preferably from one or more regions selected from the group consisting of the parahippocampal gyrus (PHG), fusiform gyrus (Fusi; area 37), dorsolateral prefrontal cortex area 9 (dlPFC), Heschl's gyrus (HG), planum temporale (PT), inferior parietal lobule (IPL), middle temporal gyrus (MTG) and primary visual cortex (V1; area 17). In some preferred embodiments of the invention where the method is used to obtain an indication of the presence of Mild Cognitive Impairment, the minicolumn-based parameters are obtained from all of these regions.

In preferred embodiments of the invention where the method is used to differentiate FTD from other dementias, the minicolumn-based parameters are obtained from or derived from one or more regions of the cortex of the brain, preferably from one or more regions selected from the group consisting of the parahippocampal gyrus (PHG), fusiform gyrus (Fusi), dorsolateral prefrontal cortex area 9 (dlPFC), Heschl's gyrus (HG), planum temporale (PT), inferior parietal lobule (IPL), middle temporal gyrus (MTG) and V1. In the most preferred embodiments of the invention where the method is used to differentiate FTD from other dementias, the minicolumn-based parameters are obtained from all of these regions.

In some preferred embodiments, the cognitive disorder is Alzheimer's Disease (AD) and the minicolumn based parameter measurements are obtained from or derived from one or more brain regions selected from the group consisting of:

(i) the banks of the superior temporal sulcus, entorhinal, isthmus cingulate, lateral occipital, lateral oribitofrontal, middle temporal, parahippocampal, parstriangularis, pericalcarine or posterior cingulate region of the left-hand cortex; and (ii) the banks of the superior temporal sulcus, cuneus, entorhinal, middle temporal, parahippocampal, paracentral or posterior cingulate region of the right-hand cortex.

In other preferred embodiments, the cognitive disorder is Alzheimer's Disease (AD) and the minicolumn based parameter measurements are obtained from or derived from the whole brain.

The regions of the brain defined herein are preferably as defined on Brodmann's cytoarchitectural organisation of the human cortex (Brodmann, 1909). The equivalents may also be seen in Von Economo and Koskinas (Von Economo C, Koskinas G N (1925) Die Cytoarchitektonik der Hirnrinde des Erwachsenen Menschen. Springer, Berlin (Germany) (Translated by Dr Lee Seldon)).

The methods of the invention may also be used to distinguish other cognitive or neuro-psychiatric disorders, as defined below. When the methods of the invention are used to distinguish the disorders recited below, the brain regions analysed should include one or more, more preferably all, of the corresponding brain regions recited below:

Autism: fusiform cortex, superior temporal sulcus, orbitofrontal cortex, dlPFC, inferior parietal cortex, primary visual cortex, primary auditory cortex Schizophrenia: dlPFC, dorsomedial PFC, cingulate gyrus, superior temporal gyrus, PHG Bipolar disorder: PHG, subgenual PFC, dlPFC, cingulate Epilepsy: entorhinal cortex, PHG Dyslexia: inferior parietal cortex, superior temporal gyrus Down's syndrome: superior temporal gyrus, PHG, dlPFC Parkinson's disease: entorhinal cortex, cingulate gyrus Amyotrophic lateral sclerosis: motor cortex Huntington's disease: motor cortex, cingulate gyrus Multiple sclerosis: motor cortex, cortical regions containing MS lesions identified by MRI scan Prion disease: primary visual cortex, cortical areas showing volumetric shrinkage contrasted with cortical area with no discernible shrinkage Depression: dlPFC, dorsomedial PFC, cingulate gyrus Obsessive-compulsive disorder: cingulate gyrus, dlPFC, dorsomedial PFC ADHD: orbitofrontal cortex, dlPFC, cingulate The subject may be any animal, preferably a mammal, most preferably a human. In some embodiments, the subject may be one with a cognitive disorder, preferably one with dementia.

In some embodiments, the subject is one which has: (i) Alzheimer's Disease (AD), (ii) cerebrovascular dementia (CVD), (iii) mild cognitive impairment (MCI), (iv) frontotemporal dementia (FTD), or (v) dementia with Lewy Bodies (DLB). Preferably, the subject has Alzheimer's disease, FTD, CVD, or MCI.

In other embodiments, the subject may be one with a neurological disorder associated with changes in normal brain structure.

In some embodiments, the subject is one which has autism, multiple sclerosis (MS), epilepsy, amyotrophic lateral sclerosis (ALS), Parkinson's disease, schizophrenia, bipolar disorder, dyslexia, Down's syndrome, Huntington's disease, prion disease, depression, obsessive-compulsive disorder or attention deficit hyperactivity disorder (ADHD).

In some embodiments, the subject is older than 1, 5, 10, 20, 30, 40, 50, 60, 70, 80 or 90 years. In other embodiments, the subject is 5-100, 10-100, 20-100, 30-100, 40-100, 50-100, 60-100, 70-100, 80-100 or 90-100 years old. In other embodiments, the subject is 1-5, 5-10, 10-20, 20-30, 30-40, 40-50, 50-60, 60-70, 70-80, 80-90 or 90-100 years old.

In some embodiments, the subject is not a foetus. The control subject may be a healthy subject or a non-healthy subject.

In some embodiments, the control may be defined as a non-diseased control, one without a cognitive disorder, a typically-developed control or a healthy-aged control. Control subjects may alternatively be called "reference" subjects.

As used herein, the term "corresponding minicolumn-based parameters or values derived therefrom" refers to a parameter or a value which is made on the same region of the brain as the one to which it is being compared, and preferably obtained under the same conditions For example, the "corresponding minicolumn-based parameters" may refer to a diffusion MRI measurement which is made on the same part of the brain as the one to which it is being compared.

Preferably, the increase or decrease is a significant increase or decrease (e.g. univariate ANOVA, $P<0.05$).

In preferred embodiments, the methods of the invention are computer-implemented methods. For example, the methods may be implemented using software.

In a further embodiment, the invention provides a system or apparatus comprising at least one processing means arranged to carry out the steps of a method of the invention.

The processing means may, for example, be one or more computing devices and at least one application executable in the one of more computing devise. The at least one application may comprise logic to carry out the steps of a method of the invention.

In a further embodiment, the invention provides a carrier bearing software comprising instructions for configuring a processor to carry out the steps of a method of the invention.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1: Microstructural Analysis of Post-Mortem Brain Tissue

Methods

TABLE 1

| Demographic summary human subjects (means and standard deviations) | | | | | |
| --- | --- | --- | --- | --- | --- |
| Diagnosis group | MMSE score | NART score | Age at death (years) | Fixation (months) | Post-mortem interval (hours) |
| CTRL, N = 20 | 28 | 118 | 81 | — | — |
| CVD, N = 18 | 25 | 116 | 81 | — | — |
| AD, N = 20 | 15 | 100 | 74 | — | — |
| FTD, N = 12 | 16 | 97 | 71 | — | — |

Subjects:

Formalin-fixed brain tissue was sampled from 58 adults (20 normal controls, 18 MCI subjects, and 20 confirmed AD patients) who had died between the ages of 59 and 101 years. (An additional set of younger control subjects was also studied, as described in the next paragraph.) The healthy controls were free from neurological or psychiatric diseases. The brains were part of the Thomas Willis Oxford Brain Collection, drawn from the OPTIMA cohort—a prospective longitudinal clinicopathological study of aging and cognitive decline. Subjects underwent cognitive testing at several time points in life. The results from the MMSE and national adult reading test (NART) were used in the present study. MCI subjects were identified as such by clinical assessment in life and did not fulfil criteria for AD at death. AD patients were confirmed with a Braak staging of V/VI at postmortem. Cases were selected from the larger Thomas Willis collection to yield comparable group mean fixation times and ages at death as far as possible, although pair matching was not possible. Demographic information per group can be found in Table 1. No comorbidity of alcohol or illicit drug misuse was detected in our sample's records. The most common causes of death were bronchopneumonia and cardiac failure. This project was carried out with approval of the UK National Research Ethics Service, study code 07/H0605/69, and informed consent was obtained from all subjects and family representatives. Brains were bisected and assigned a randomized code by a third party so that measurements could be made blind to diagnosis. Only the left cerebral hemisphere was available for study, and this was fixed in 10% formalin. Samples from different brain regions were taken for confirmation of diagnosis according to the criteria of the Consortium to Establish a Registry for Alzheimer's Disease (CERAD) and assigned a Braak score. Brains that showed substantial signs of other pathology, including Creutzfeldt-Jacob disease, Parkinson's disease, Lewy body disease, Huntington's disease, cerebrovascular disease, and brain tumours, were excluded.

CVD cases from the OPTIMA cohort were defined as having dementia associated with cerebrovascular disease including a combination of small vessel disease, microinfarcts, atherosclerosis (in two cases there was evidence of large vessel infarction) and a Braak NFT stage of I/II or less with absence or very sparse presence of neuritic plaques in frontal, temporal and parietal lobe neuropathological samples. FTD cases were demonstrated to be TDP-43 positive with limited AD pathology (most cases had no AD pathology, 3 cases had minor AD pathology (Braak stage I/II, no plaques) and one case had notable AD pathology (Braak stage V/VI, sparse plaques)). These cases also had no evidence of notable cerebrovascular disease, including no evidence of large vessel infarcts, microinfarcts, and absent or mild: atherosclerosis, small vessel disease, and amyloid angiopathy. The subjects had received a diagnosis of frontotemporal lobe dementia or, in three cases, a diagnosis of frontal lobe dementia with motor neuron disease-type inclusions (Parkinson's disease was excluded).

AD, MCI and control subjects were the same as those reported in previous studies (Chance et al., Van Veluw et al.).

Neuropsychology:

Subjects underwent regular neuropsychological testing in life (typically every 6 months). Three neuropsychological test scores were used to look for anatomical correlates in the present study. MMSE scores were used as a standard assessment for overall memory and cognitive decline that is in common clinical use. NART score was used because it has been shown to be a reliable premorbid IQ estimation (McGurn et al. 2004). Another global cognitive decline assessment, Cambridge cognitive examination (CAMCOG) score was also considered but was not included in further analysis because it so closely resembled MMSE score (Pearson's r=0.98; p\0.01) in all respects and it did not add anything further to the analysis.

Tissue Sampling and Processing:

The regions of interest (ROIs) comprised five brain areas. These included two regions for which correlations between minicolumn organisation and cognitive scores have been reported previously in AD (Van Veluw et al.), dorsolateral prefrontal cortex Brodmann's area 9 (dlPFC, BA9) and the Planum Temporale (PT). Data from the primary auditory region within Heschl's gyrus (HG) were also included, which have been reported previously for AD (Chance et al.). In addition, data were collected from ventral/medial temporal lobe regions: the parahippocampal gyrus (PHG) and, for a subset of cases, the fusiform gyrus (Fusi).

An overall clinical neuropathological rating for plaque and tangle pathology was provided on the Braak staging scale. In addition a quantitative histological assessment was conducted to estimate more precisely the tangle density and plaque load in three regions representative of the three broad areas under investigation in this study: medial temporal lobe, superior temporal lobe, and prefrontal cortex.

The dlPFC was sampled by taking blocks of tissue containing the superior frontal gyrus from the middle of the left hemisphere. The anterior and posterior limits of the dlPFC ROI were defined with reference to landmarks on the medial surface of the hemisphere—the posterior limit was formed by a vertical line drawn from the front edge of the genu of the corpus callosum and the anterior limit was vertical from the anterior apex of the paracingulate sulcus. A 5-mm thick sample block was dissected from the dorsal brain surface within these bounds, descending laterally to the limit of the superior frontal gyrus. The PHG was sampled within an ROI as defined elsewhere (McDonald et al. 2000). In summary, the limits of the ROI were given by the posterior boundary, defined as the most posterior part of the hippocam pus, the anterior boundary defined as the point where the hippocam pus merges with the amygdala, and the superior boundary was the fusion between the hippocam pus and the subiculum. The blocks were taken from randomized positions with respect to the anterior and posterior boundaries of both ROIs. For sectioning, blocks were cryopro- tected by immersion in a 30% sucrose solution for 4 weeks, during which the solution was regularly refreshed. Then they were frozen and stored at −80° C. A cryotome was used to cut 30-lm thick sections for slide mounting. For visualizing neurons (to measure minicolumn width) sections were Nissl stained with cresyl violet. Each ROI was analyzed on two non-contiguous slides (slides were separated by up to 5 mm within the ROI). Serial sections between the minicolumn sections were also taken to quantify the extent of plaques and tangles using methanamine silver stain and AT8 immu- nohistochemistry.

Tissue Staining and Immunohistochemistry:

To demonstrate senile plaques in the dIPFC and PHG of the elderly subjects (excluding the young control group), a methenamine silver stain was applied to 30-lm thick sections heated in solution in the oven for 90 min at 60° C. Cresyl violet (0.1%) was used for counterstaining. To assess tangle pathology in both the dIPFC and PHG, 30-lm thick sections were reacted with phosphorylation-dependent antitau mono- clonal mouse antibody AT8 obtained from Innogenetics. A primary antibody concentration of 1:1,500 was incubated for 60 min at room temperature. HRP rabbit/mouse secondary antibody was applied for 45 min, and staining was visualized using nickel-enhanced diaminobenzidine with hematoxylin counterstain.

Image Analysis

Plaque load was assessed and tangles were counted as described for a previous study (Chance et al. 2011). In short, plaque load was calculated by taking the percentage of intact tissue covered by plaques, by counting grid points on four digital photomicrographs of the ROI using a standardised search pattern. Tangles were counted using multiple place- ments of a 640 9 400 lm counting frame on live computer- ized microscope images using an alternative search pattern. Tangle density was calculated per $mm^2$ from combined pyramidal cell layers III and V. Minicolumn width was quantified using semi-automated image analysis. This method and its validation have also been described in detail previously (Casanova and Switala 2005; Buxhoeveden et al. 2000). In summary, minicolumn width is calculated from the combined width of the dense core region plus the associated peripheral neuropil-space around the core. The minicolumn is taken to consist of both around the core. The minicolumn is taken to consist of both the core and its periphery. It is worth noting that, as in our previous reports (e.g. Chance et al. 2006a, 2011; Di Rosa et al. 2009), the measure is effectively an estimate of centre-to-centre spacing of mini- columns. Although some studies define width as only the width of the core, and spacing as only the space between cores, the designation of these boundaries tends to be less clear than the periodicity from centre-to-centre, which is the measure most easily related to the wider literature (Peters 2010). For measurements, two sections from each ROI were used for sampling. Four pictures were taken for each subject in each ROI, with each micrograph containing a region about 1 $mm^2$ in area. Fields of view were selected by a random search pattern that excluded regions of high cortical curvature such as the fundi of sulci or the apices of gyri [although minicolumns are still clearly visible, high curva- ture affects cell distribution (Chance et al. 2004)]. Minicol- umns are clearest in layer III, so minicolumn detection was centred on that layer. Photographs were obtained through a 49 objective lens, with an Olympus BX40 microscope (FIG. 1) [more details can be found in Di Rosa et al. (2009) and Chance et al. (2004)].

Statistical Analysis:

Statistical analysis was conducted using SPSS software (version 17.0). One-way ANOVAs were used to compare main effects for dIPFC and PHG plaques and tangles, dIPFC and PHG minicolumn width, and neuropsychological scores in the sample groups. Levene's test of homogeneity of variance was used to assess the equality of variances. Where a main effect was found, we looked at differences of means between groups using independent samples t tests. As post hoc tests we used Fisher's least significant difference (LSD), or Dunnett's T3 test in the case of a non-homogenous distribution of the data. Paired samples t tests were used to compare pathology (plaques and tangles) in each diagnostic group and repeated measures ANOVAs were used to confirm the findings as revealed by the t tests. Furthermore, the relationships between IQ and MMSE scores were compared using Pearson's correlation analysis. The effect of age on minicolumn width was also assessed by Pearson's correla- tion in normal aging subjects. An independent samples t test was used to explore pathological differences in AD patients when we divided the group in high and low IQ scores. Potential covariates were identified as age at death, fixation time, post-mortem interval, and total brain weight. Of these, brain weight (F=8.23; df=2, 55; p\0.01) and age at death (F=7.62; df=2, 55; p\0.01) differed between groups. There- fore, the influence of these two covariates was always tested by incorporating them into the ANOVAs.

Age is significantly different for both CTRL and CVD group compared to either the AD or FTD group.

Results

Cerebrovascular Disease

Demographics:

Brain weight was significantly different between diagnos- tic groups (univariate ANOVA; F=6.1, df 3,72, P<0.01); brains were heavier in controls than MCI and CVD, and all groups were heavier than the AD cases. Age at death was significantly different between diagnostic groups (univariate ANOVA; F=6.3, df 3,75, P<0.01), mainly due to the AD cases having died at a younger age than cases in the other groups. Post-mortem interval did not differ between groups (F=1.4, df 3,70, p=0.24) and fixation time did not differ between groups (F=0.8, df 3,75, p=0.53); therefore, these were not included as covariates in subsequent ANOVAs.

Minicolumn Measures:

Minicolumn measures passed Kolmogorov-Smirnov tests for normal distributions; therefore repeated measures ANO- VAs were applied to these data. Pillai's trace criterion was used within these tests due to a low Box's M-Test result for homogeneity of variance (P<0.05) (although this did not fall below the critical P=0.001 level). There was a significant main effect of diagnosis (Pillai's trace, F=4.0, df 3,60, P=0.01) and a significant interaction between diagnosis and brain region (Pillai's trace, F=3.7, df 12, 177, P<0.01) for measures of minicolumn width. Post-hoc t-tests clarified the effects: minicolumn widths in all brain regions were reduced in AD compared to controls (P<0.05 for all cortical regions). In CVD, minicolumn width was reduced in two brain regions; prefrontal cortex (t=2.3, df 35, P<0.05) and para- hippocampal gyrus (t=3.6, df 32, P<0.01) compared to controls. Differentiating CVD from AD, minicolumn width was preserved in fusiform cortex in CVD (significantly wider than AD; t=5.4, df 32, P<0.01) and there was a trend for preserved minicolumn width in the Planum Temporale in CVD (wider than AD; t=1.7, df 34, P<0.1). In these post-hoc tests of the separate brain regions, MCI cases did not have significantly reduced minicolumn width for any one region compared with controls (although it has been shown previously that an overall reduction is detected in these MCI cases when a combined statistical test is applied to multiple regions, including PT, PHG and PFC (Van Veluw et al 2012)). Compared to MCI, the AD cases had reduced minicolumn width in PFC (t=4.3, df 36, P<0.01), fusiform (t=5.0, df 33, P<0.01) and a borderline reduction in Heschl's gyrus (t=1.6, df 36, P=0.06), whereas minicolumns were thinned enough in the PHG and PT that for these regions MCI cases did not significantly differ from AD.

Brain weight was a significant covariate (F=7.8, df 1,60, P<0.01) and so was included in the rmANOVA (although it showed no other significant interactions). Age was not a significant covariate (F=0.08, df 1,59, P=0.78) and did not significantly affect the other data interactions and so it was not included in the main rmANOVA.

Neuropathological Markers:

Measurements of plaques and tangles in the control, MCI and AD subjects in this study have been reported previously for the three brain regions investigated. However, further analysis is reported here for comparison with the two new groups of cases: CVD and (see below) FTD. Measurements of plaques and tangles failed Kolmogorov-Smirnov tests for normal distributions due to a floor effect where many subjects had values close to zero in all diagnostic groups except AD (the AD group passed this test for data from all three brain regions). Therefore, non-parametric tests were used for group comparisons:

Neuritic Plaques

The % cortical area covered by plaques (described here as C '% plaque area') was significantly different between diagnostic groups for each of the superior temporal lobe, medial temporal lobe and prefrontal cortex (independent samples Kruskal-Wallis tests for all regions P<0.01). Post-hoc Mann-Whitney tests confirmed that AD subjects had greater % plaque area in all three brain regions compared to controls and to CVD cases. MCI was intermediate between these groups with higher plaque load in the medial temporal lobe than both controls (U=34.0, Z=−4.2, P<0.01) and CVD (U=2.0, Z=−4.8, P<0.01) but no difference from controls or CVD in the prefrontal cortex or superior temporal lobe regions.

Overall, AD had elevated plaque load in all areas, whereas CVD had relatively low plaque load similar to controls. MCI looked intermediate with elevated plaque load similar to AD in the medial temporal lobe but lower plaque load similar to CVD and controls in the other regions.

Neurofibrillary Tangles

The number of tangles/mm$^2$ was significantly different between diagnostic groups for each of the superior temporal lobe, medial temporal lobe and prefrontal cortex (independent samples Kruskal-Wallis tests for all regions P<0.01). Post-hoc Mann-Whitney tests indicated that AD cases had a greater density of tangles in all three brain regions compared to controls, MCI and CVD (all P<0.01). CVD cases also had more tangles in all three regions compared with controls (all regions P<0.05), while MCI only had more tangles compared with controls in one region: PHG (U=74.5, Z-3.2, P<0.01). The selective vulnerability of the PHG in MCI was also notable because for this region the density of tangles was greater than in CVD cases as well (U=101.0, Z=−1.9, P=0.05), whereas for the other two regions tangle density was slightly greater in CVD (although statistically not significant).

Fronto-Temporal Dementia

Unfortunately, ventral and medial temporal lobe tissue samples were not available for minicolumn analysis in the majority of FTD cases. Therefore, only regions PFC, PT and HG were included in the analysis of FTD minicolumns. Minicolumn data passed Kolmogorov-Smirnov tests for normal distributions and Box's M-Test result for homogeneity of variance, therefore rmANOVA was applied.

Demographics Including FTD:

Brain weight was significantly different between diagnostic groups (univariate ANOVA; F=12.0, df 4,85, P<0.01); brains were heavier in controls compared with all groups, AD cases and FTD cases were lighter than controls, MCI and CVD, and FTD cases weighed less than all other groups. Age at death was significantly different between diagnostic groups (univariate ANOVA; F=7.7, df 4,87, P<0.01), due to the AD and FTD cases having died at a younger age than subjects in the other groups. Fixation time did not differ between groups (F=1.4, df 4,87, p=0.24) and, therefore, was not included as a covariate in the main rmANOVA. Postmortem interval also did not differ between groups (F=2.1, df 4,79, p=0.09), although because this was a weak trend (i.e. P<0.1) it was tested for significance as a covariate. PMI was not a significant covariate (F=2.4, df 1,64, P=0.13) and as it did not markedly affect the significance of the other data interactions it was not included in the main rmANOVA. Age was also not a significant covariate (F=0.6, df 1,72, P=0.43). However, because the FTD subjects died at a significantly younger age than the other groups except for AD, its effect in the rmANOVA was investigated and its inclusion did influence other data interactions (see below). Brain weight was a significant covariate (F=5.7, df 1,73, P<0.05) and so was included in the rmANOVA (although it showed no other significant interactions).

Minicolumn Measures:

There was a significant interaction between diagnosis and brain region for measures of minicolumn width (F=4.1, df 4,73, P<0.01), and a trend for a main effect of diagnosis (F=2.2, df 4,73, P=0.08). Pillai's trace criterion also revealed a trend for an overall difference between brain regions. However, inclusion of age as a covariate, while not a significant covariate (see below), resulted in the loss of this trend (F=0.7, df 2,71, P=0.52), although the interaction between diagnosis and brain region remained (F=2.4, df 8,144, P<0.05).

Post-hoc tests confirmed a pattern of contrasts distinguishing FTD from the other groups except AD. There was minicolumn thinning compared with controls in prefrontal (t=3.7, df 28, p<0.01) and temporal lobe association cortex (t=2.2, df 30, p<0.05) but not in primary auditory region HG. Compared with MCI and CVD the thinning in FTD was only notable for prefrontal cortex (MCI vs FTD: t=4.7, df 26, p<0.01; CVD vs FTD: t=2.4, df 25, p<0.05). Compared with AD the minicolumn widths in these three brain regions did not differ from FTD cases, although there was a trend for greater thinning in AD in the HG cortex (t=1.7, df 27, p=0.09).

Neuropathology:

As already established for group comparisons with cerebrovascular disease, the % plaque area and the density of tangles/mm$^2$ also differed between diagnoses with the inclusion of the FTD data (all measures P<0.01). Post-hoc tests identified that FTD had similar levels of these pathological markers to CVD cases (although with a trend for a higher density of tangles/mm$^2$; Mann Whitney U=74.5, Z=−1.7, p=0.09) and all markers were lower for FTD than for AD (all measures P<0.01). FTD cases had lower levels of neuropathological markers in PHG than MCI cases (both plaque area, U=2.0, Z=−4.4, p<0.01, and tangle density, U=42.5, Z=−2.6, P<0.01) and lower plaque area in PT (U=50.0, Z=−2.5, p<0.05). Compared with controls, plaques and tangles were not different in FTD except for PHG where % plaque area was greater in controls (U=59.0, Z=−2.2, P<0.05).

Correlation Analysis

Overall correlations were tested across all subjects followed by post-hoc tests to determine the extent of the relationships within diagnostic groups:

Age:

For minicolumn width, only prefrontal cortex showed a correlation with age across all cases (r 0.31, p<0.01) (subjects who died at an older age had wider minicolumns). No other regions showed this effect. However, within diagnostic groups the CVD cases differed from others in having negative relationships between age and both fusiform minicolumn width (r −0.68, p<0.01) and PHG minicolumn width (r −0.53, p=0.05) (minicolumn thinning in old age).

For neuropathological markers across all cases age was only negatively correlated with tangle density in STG (r −0.34, p<0.01). Further post-hoc investigation confirmed that age was only correlated with tangle density in AD cases (older subjects had lower tangle density) in the STG (r −0.65, p<0.01) and in PHG (r −0.64, p<0.01).

Donors who died at an older age also had higher MMSE (r 0.55, p<0.01) and IQ (r 0.36, p<0.01) scores. Within diagnostic groups the relationship with IQ score was positive for both the control (r0.50, p<0.05) and the AD (r 0.48, p<0.05) groups.

Brain Weight:

Heavier brains were associated with wider minicolumns for all brain regions across the total dataset. Within the control group, HG was the only brain region in which this relationship held true (r 0.54, p<0.05) and no relationship was found for fusiform cortex or other associative brain regions. The CVD cases differed from MCI and AD cases in exhibiting a positive relationship between PT minicolumn width and brain weight (r=0.53, p<0.05) and HG minicolumn width and brain weight (r=0.55, p=0.05), whereas MCI showed a positive relationship between fusiform minicolumn width and brain weight (r=0.55, p<0.05) and AD exhibited a similar trend (r=0.050, p=0.06).

For neuropathological markers across all cases, greater brain weight was associated with fewer neurofibrillary tangles in PHG (r=−0.30, p<0.01) and PFC (r=−0.23, p<0.05). No other correlations were found. Further post-hoc analysis within diagnostic groups did not find correlations between brain weight and any pathological markers. Across all cases, donors with larger brains had higher MMSE (r=0.56, p<0.01) and IQ (r=0.40, p<0.01) scores. Post-hoc investigation within diagnostic groups found that this relationship was only consistent in the AD group (MMSE: r=0.57, p<0.01; IQ: r=0.52, p<0.02).

Minicolumns and AD Pathology:

Across all subjects and within each brain region % plaque area and tangle density were positively correlated with each other. Within diagnostic groups % plaque area in the STG was correlated with % plaque area in PFC. This was true for CVD cases (r=0.65, p<0.01) where there was also a correlation between STG tangle density and PFC tangle density (r=0.70, p<0.01). The degree of pathology in MTL was less consistently correlated with other variables, exhibiting no relationship in CVD, whereas in FTD the PFC plaques and tangles were highly correlated with each other (r=0.95, p<0.01) and with MTL % plaque area (PFC plaques: r=0.92, p<0.01; PFC tangles: r=0.98, p<0.01).

In prefrontal cortex wider minicolumns were associated with lower % plaque area (as reported previously; Van Veluw et al 2012). The other region which showed a similar link between minicolumn width and pathology was fusiform cortex where narrower minicolumn width was associated with increased plaques and tangles in the medial temporal lobe and the other regions (MTL and PFC). Within diagnostic groups these effects were mainly found in AD where increased % plaque area was associated with reduced minicolumn width in both the PHG (r=−0.47, p<0.05) and PFC (r=−0.47, p<0.05). One notable contrasting relationship was found in the FTD group where the relationship between minicolumn width and pathology in PFC was in the opposite direction (positive) for both plaques (r=0.70, p<0.05) and tangles (r=0.68, p<0.05).

Across all cases, minicolumn widths in PFC and PT were correlated with each other (r=0.48, p<0.01). Within diagnostic groups this was found in controls (r=0.54, p<0.05) as well as in MCI, AD and CVD. By contrast, although minicolumn widths in PHG and fusiform were also correlated with each other across all cases (r=0.37, p<0.01), this was due to correlations in the dementia groups (CVD: r=0.66, p<0.05; AD: r=0.80, p<0.01) and was not found in controls (r=0.04, p=0.89) or MCI (r=0.39, p=0.13).

Neuropsychology and Neuropathology

Across all subjects, as reported previously for PFC, PHG, and PT (refs), wider minicolumns in fusiform cortex were correlated with higher cognitive scores; MMSE (r=0.46, p<0.01) and IQ (r=0.28, p<0.05). Within diagnostic groups this effect was mainly found in AD where minicolumn thinning in fusiform cortex was associated with lower MMSE (r=0.47, p<0.05) and lower IQ score (r=0.6, p<0.01). By contrast, in CVD, this relationship did not hold and the minicolumn width in the fusiform cortex and in all other brain regions was mildly (although not significantly) negatively associated with cognitive scores. For FTD there were no apparent relationships between cognitive scores and minicolumn width in any regions.

For % plaque area and tangle density in PHG, STG and PFC (i.e. all of the regions where neuropath markers were measured) there were significant negative correlations with MMSE score across all cases. There were also negative correlations with IQ for tangle density in all regions, while for % plaque area the negative relationship was only clear for STG (r=−0.25, p<0.05). Within diagnostic groups relationships between higher tangle density and lower test scores (both MMSE and IQ) were found in the AD group, specifically related to the pathology in the PHG (MMSE: r=−0.62, p<0.01; IQ: r=−0.52, p<0.05), in the CVD group, specifically related to tangles in the STG (IQ: r=−0.52, p<0.05).

Example 2: Predictive Modelling

The same data used as in Example 1 but a different form of statistical analysis was applied, i.e. leave-one-out cross-validation which predicts the status of one case on the basis of the model derived from all other cases and then repeats this process for all cases, resulting in a final analysis of the predictive value of the discriminant function model derived from the whole dataset for all cases in the dataset. It is a standard form of analysis, conducted using SPSS statistical software in this case.

Discriminant function analysis was used to generate predictive models to categorise cases into diagnostic groups. This is of interest to determine the differential diagnosis potential of multi-region minicolumn data that may provide sensitivity and specificity estimates as a target for neuro-imaging methods in living subjects. Discriminant function analysis was conducted with SPSS to investigate early diagnosis potential (controls, mild cognitive impairment (MCI) and Alzheimer's disease (AD)) and differential diagnosis (AD, cerebrovascular dementia (CVD), and fronto-temporal dementia (FTD)).

Figure 7:
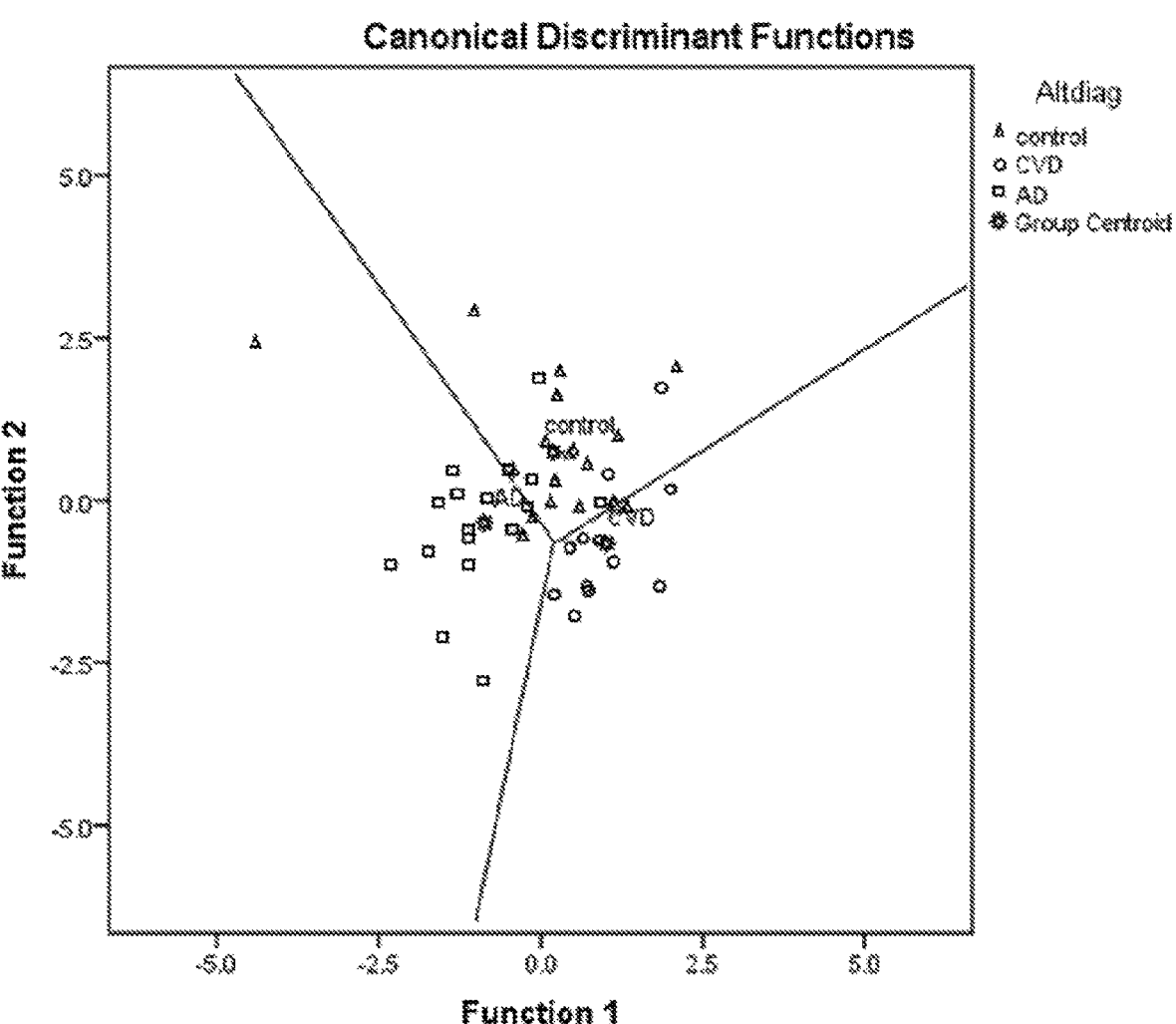
FIG. 7 shows the resulting map with predictive group centroids and territories from the discriminant analysis conducted using minicolumn widths from five brain regions: PFC, HG, PT, PHG, and Fusi to compare controls, CVD and AD.

Differential Diagnosis, AD Vs Cerebrovascular Disease:

A discriminant analysis was conducted using minicolumn widths from five brain regions: PFC, HG, PT, PHG, and Fusi to compare controls, CVD and AD. The resulting map with predictive group centroids and territories is shown in FIG. 7.

The analysis correctly classified 75% of the original group cases. PFC, Fusi, and PHG significantly differed between the groups (p<0.05 each). Function 1 had a canonical correlation of 0.61, with Wilks' Lambda 0.46, p<0.01, and Function 2 had a canonical correlation of 0.53, with Wilks' Lambda 0.72, p<0.01. A leave-one-out cross-validation analysis found just over 65% of cases correctly classified.

This model is interesting although it resulted in some overlap between controls and each of the other diagnoses. The graphical analysis demonstrates that group separation is promising, perhaps with the addition of further brain region data. In addition, the control territory lying between AD and CVD indicates that the CVD data is not a mildly affected intermediate between AD and controls but has a different pattern of change from the other two groups.

Most interesting of all is that the AD and CVD groups are almost entirely separated. This is particularly important for differential diagnosis. Most of the inaccuracy in the model is due to overlap with controls. However, if the clinical decision of interest concerns the differential diagnosis of AD and CVD then a follow on discriminant analysis looking at just these two groups is highly informative—such an analysis was found to correctly classify 97% of the two diagnostic groups. The canonical correlation was 0.87, Wilks' Lambda 0.24, p<0.001 (Box's M was acceptable with a p-value >0.01) A leave-one-out cross-validation analysis found remarkably high predictive accuracy with just over 93% of cases correctly classified. The only case m is-classified was a single AD case that was predicted to be CVD, leaving 100% correct classification of CVD cases. This model has enormous potential for further application in imaging studies.

Early Detection (MCI):

A discriminant analysis comparing normally aged controls with mildly cognitively impaired cases (MCI) was conducted to estimate the potential for early detection before the diagnosis of dementia. Using the five brain regions mentioned above the analysis generated a model that correctly classified 72% of the original grouped cases. The leave-one-out cross validation test indicated correct classification of 64%.

Classifying Frontotemporal Dementia:

A discriminant analysis of data from all regions resulted in the inclusion of too few members of the FTD group to be meaningful and such an analysis became dominated by the AD and CVD data. However, it may be noted that the remaining cases of FTD were classified as CVD suggesting potential separation from AD diagnosis which would be of great interest to assist clinical practice as, currently, differential diagnosis of FTD from AD is very challenging. Therefore a discriminant analysis was focused on the most meaningful clinical contrast—the contrast between FTD and AD—using the three brain regions that were available for the majority of these cases: PFC, HG, and PT. This analysis found that 71% of the original group cases were correctly classified with leave-one-out cross validation correctly classifying 68% of cases.

The correct differential prediction of AD cases was good at 90% with only 10% mis-classified as FTD. However, the prediction of FTD group membership was poor with more than half m is-classified as AD. It is likely that greater accuracy would result from the inclusion of data from more brain regions including the regions that were missing here: Fusi and PHG.

Preliminary Data from Post-Mortem MRI Using Diffusion Imaging of Cortex:

This analysis extracted one of the measures that has potential as an index of minicolumn structure in diffusion MRI ('perpendicular diffusion'). This measure was extracted from post-mortem images and then compared with histological measurements from the same brain regions following dissection and microscope slide analysis.

Figure 8A:
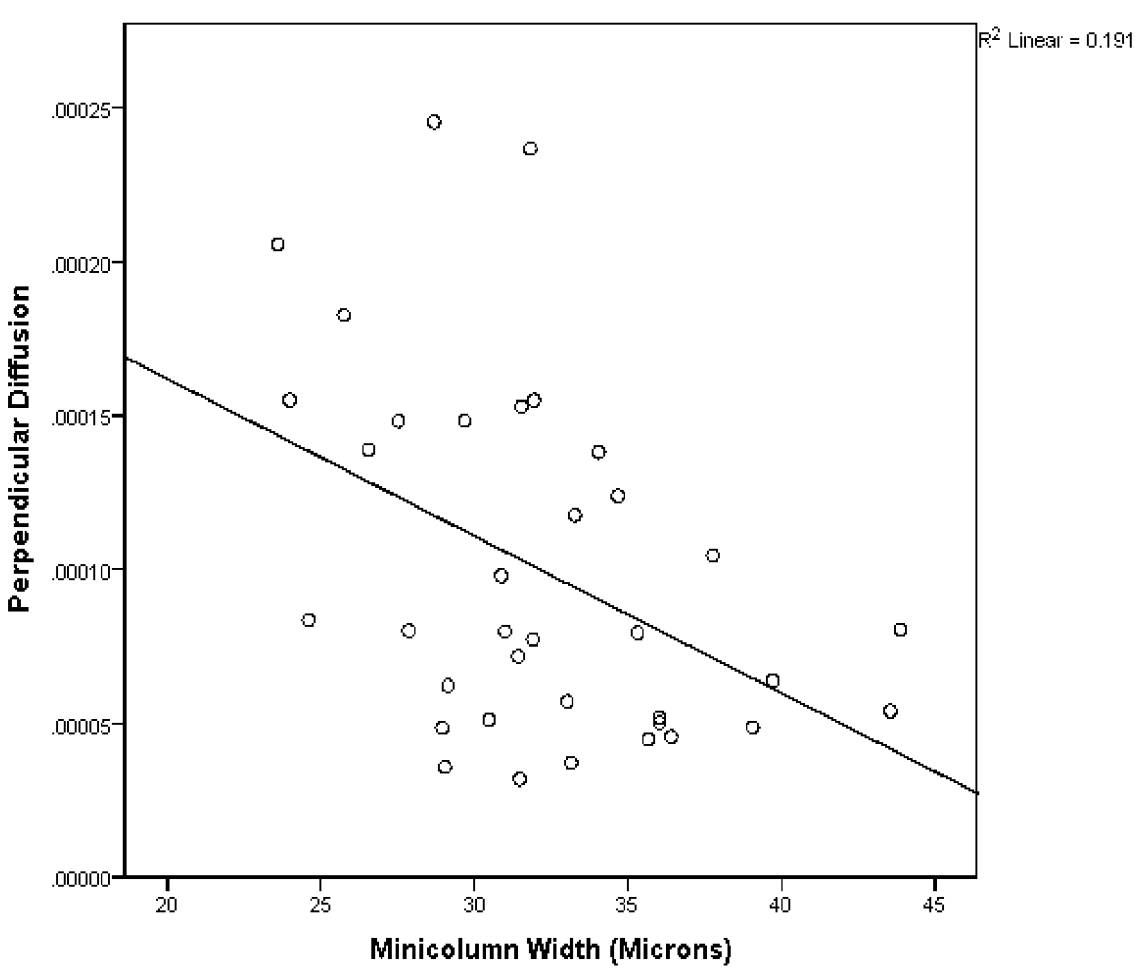
FIG. 8A shows a graph of data from post-mortem non-dementia brains (including controls, MS and autism) demonstrating that wider minicolumns are associated with a lower perpendicular diffusion measure.

FIG. 8A shows a graph of pilot data from post-mortem non-dementia brains (including controls, MS and autism)—wider minicolumns are associated with a lower perpendicular diffusion measure. The prediction for AD is that minicolumn thinning will lead to an increase in the perpendicular diffusion measure.

Figure 8B:
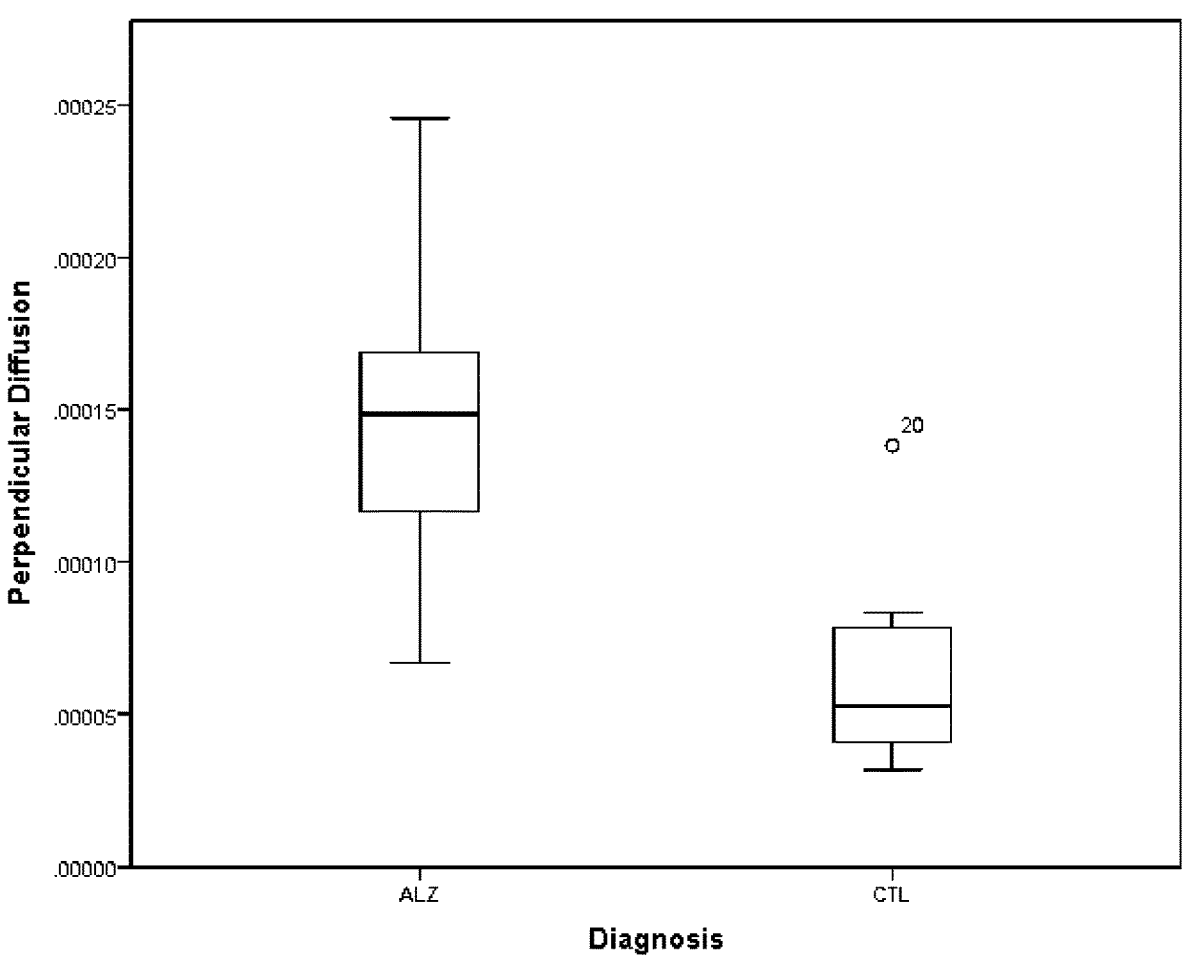
FIG. 8B shows pilot post-mortem imaging reveals an increased perpendicular diffusion measure in dementia consistent with minicolumn thinning (p=0.05, n=4 AD vs 4 controls).

FIG. 8B shows our recent pilot post-mortem imaging reveals an increased perpendicular diffusion measure in dementia consistent with minicolumn thinning (p=0.05, n=4 AD vs 4 controls).

Figure 8C:
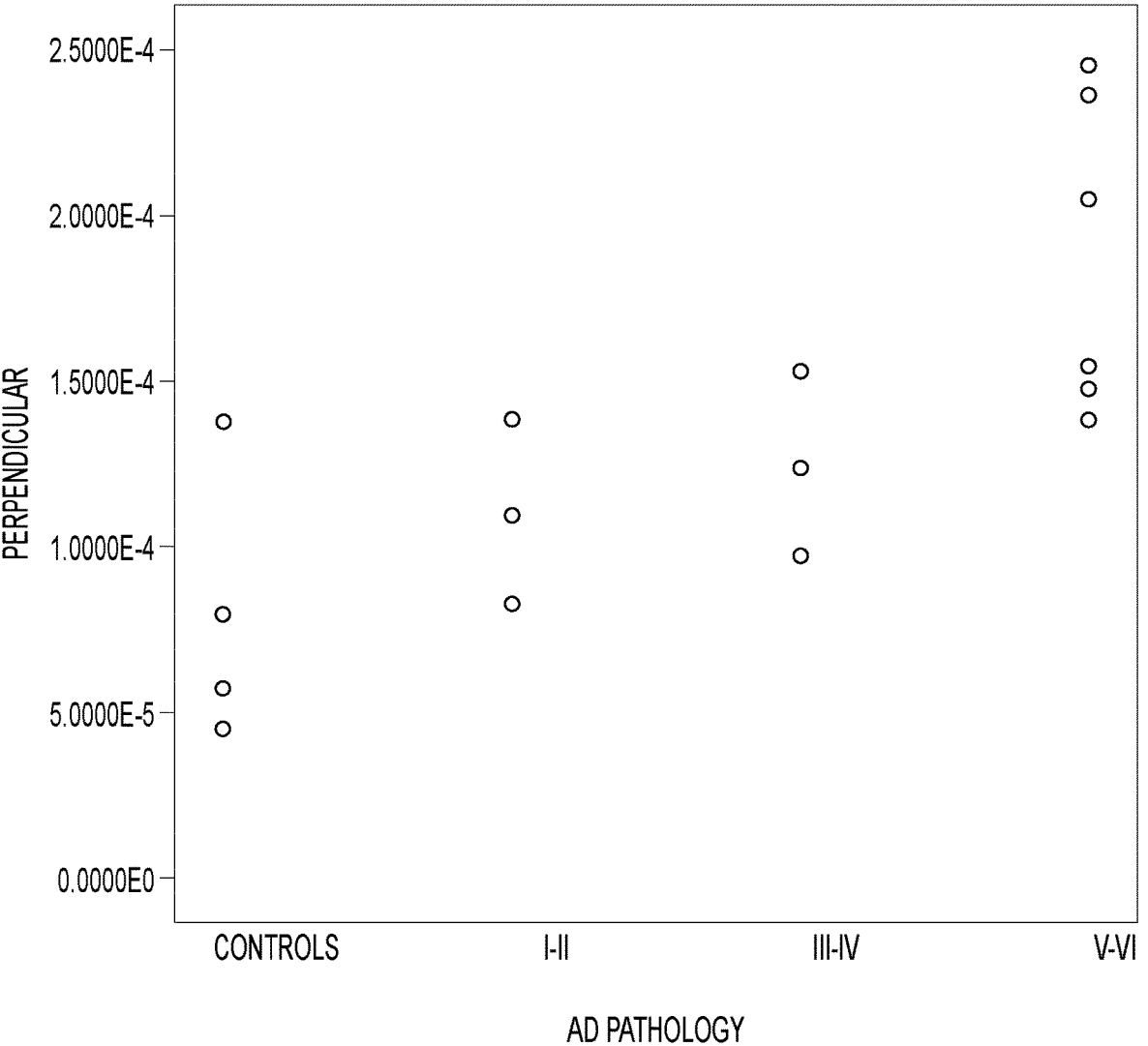
FIG. 8C shows that the DTI biomarker has a graded effect reflecting the degree of AD pathology—values increase with greater severity of AD pathology. (Data are mean values for 4 control subjects and individual sub-regions values from 4 probable AD brains—sub-regions PHG, HG, and PT show a characteristic pattern of differences).

FIG. 8C: the DTI biomarker shows a graded effect reflecting the degree of AD pathology—values increase with greater severity of AD pathology. (Data are mean values for 4 control subjects and individual sub-regions values from 4 probable AD brains—sub-regions PHG, HG, and PT show a characteristic pattern of differences).

Example 3: Data from In Vivo MRI
Scanning—Using Mean Diffusivity

This data was extracted from previously gathered MRI data in another study which was not optimal for this analysis (lower resolution data acquisition) but was intended to give a sense of potential for gathering in vivo data. This provided mean diffusivity data (which is likely to be a less sensitive indicator of minicolumn organisation than the measures mentioned above) from in vivo MRI of subjects in two diagnostic categories: MCI and healthy aged controls.

A discriminant analysis was conducted on data gathered from a small set of brain regions involving PHG, HG, and Fusi. The statistical model found that 71% of the original cases were correctly classified with a leave-one-out cross validation accuracy of 58%. Although these models are not as effective as the post-mortem MCI categorisation it is highly likely that they would improve if further work was done to acquire higher resolution in vivo data using the a more promising signal marker such as 'perpendicular diffusion'.

Figure 9:
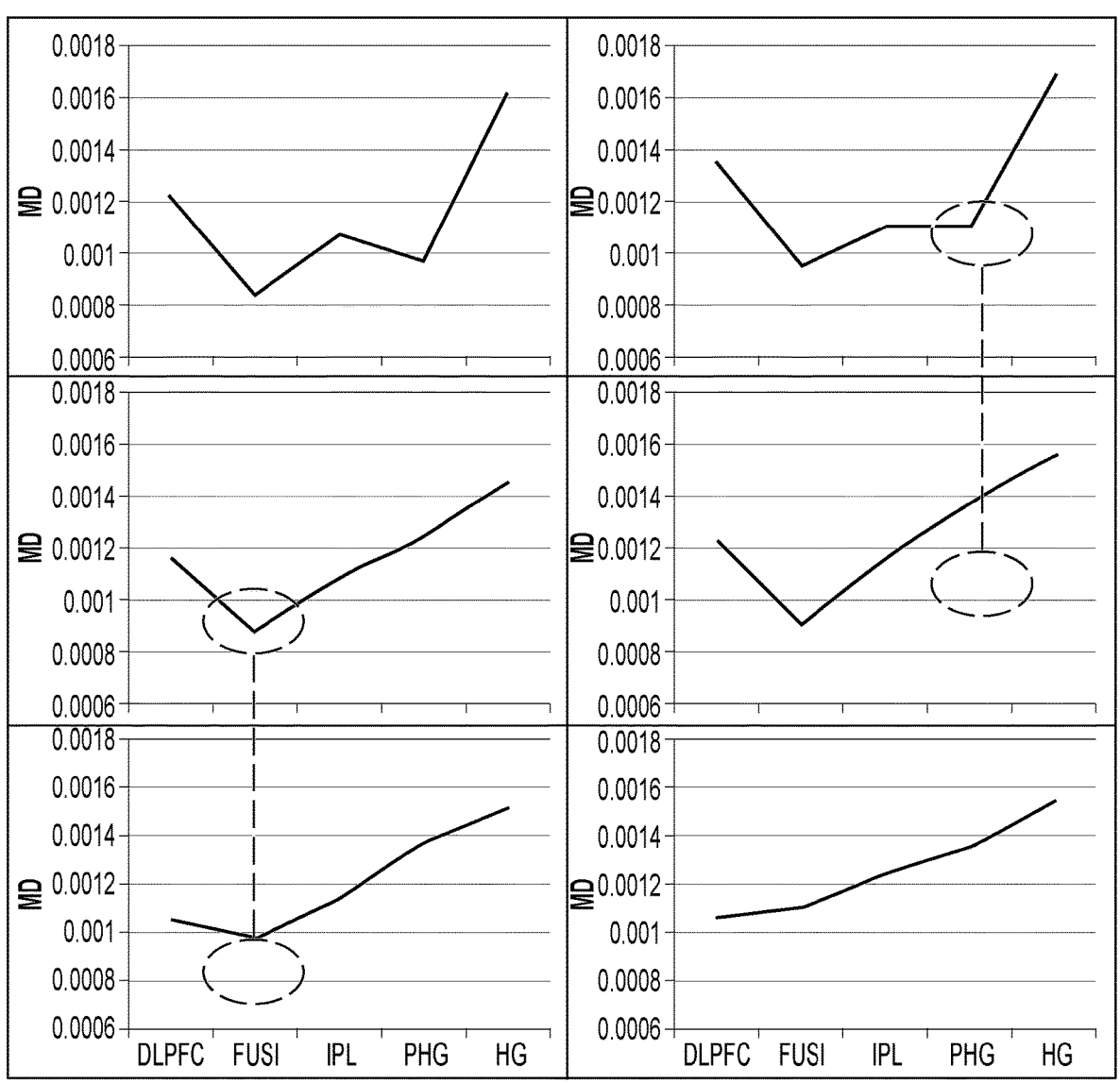
FIG. 9 shows pilot in vivo cortical diffusion data (mean diffusivity) from 6 subjects. Each graph shows cortical diffusivity (MD) for 5 regions from a single subject. Top row: graphs from 2 Control subjects, Mid row: graphs from 2 MCI subjects, Bottom row: 2 AD subjects. The PHG feature in the pattern (orange contrast) differentiates controls from MCI, the Fusi feature (yellow contrast) differentiates AD from MCI.
Figure 10:
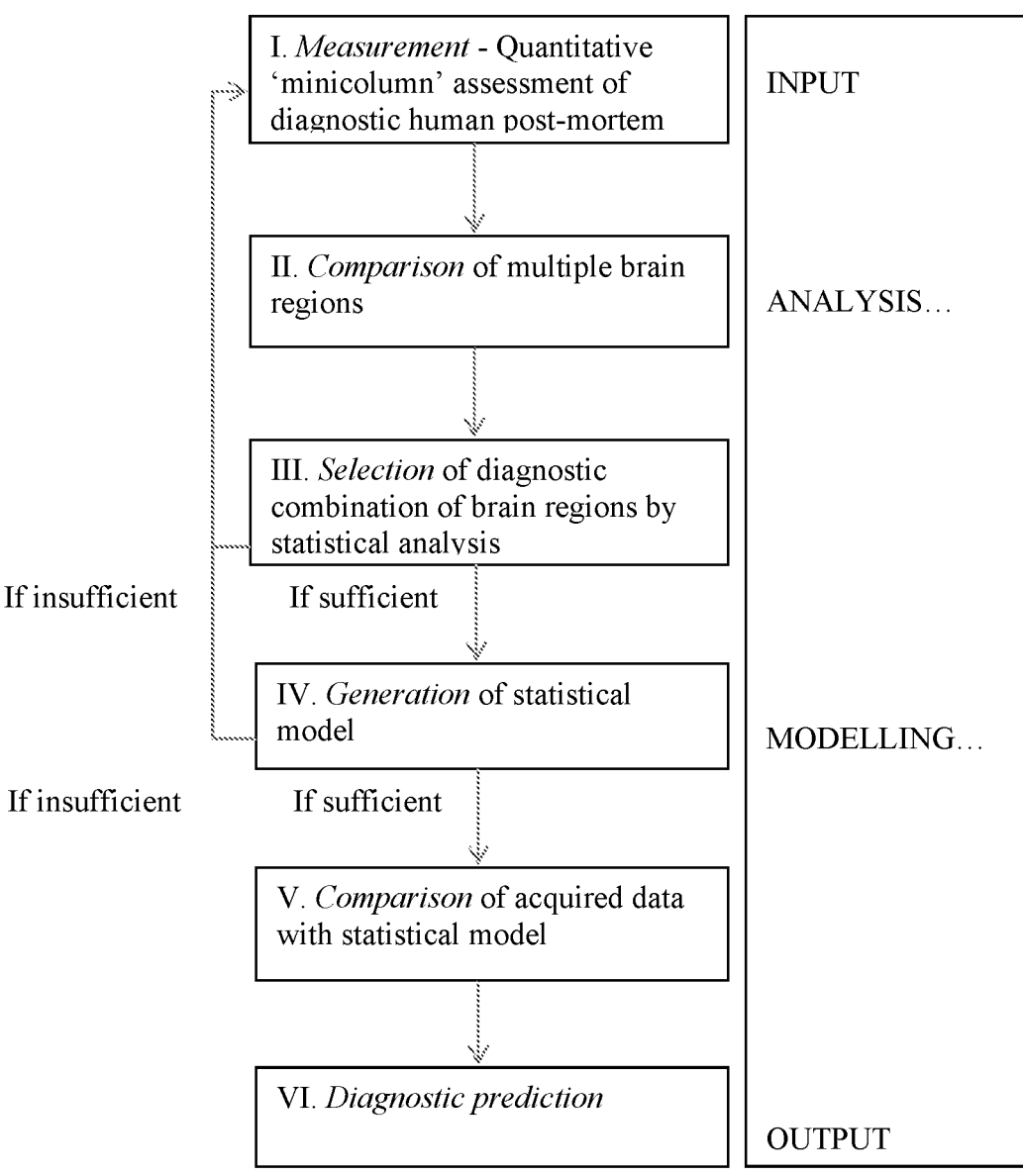
FIG. 10 shows a flow chart illustrating an algorithm for early and differential diagnosis of dementia and other brain disorders.

Pilot in vivo cortical diffusion data (mean diffusivity) from 6 subjects shows patterns within single subjects that are more similar within groups than between groups and are not only dependent on group statistics (see FIG. 9). The strongest signature for optimal sensitivity and specificity should be predicted by the post-mortem microanatomical patterns described above. Each graph shows cortical diffusivity (MD) for 5 regions from a single subject. Each pair of graphs shows a similar pattern that differs from the patterns in the other rows. Top row: graphs from 2 Control subjects, Mid row: graphs from 2 MCI subjects, Bottom row: 2 AD subjects. The PHG feature in the pattern (orange contrast) differentiates controls from MCI, the Fusi feature (yellow contrast) differentiates AD from MCI. In addition, most values increase from control to AD.

Example 4: Diagnosis of Alzheimer's Disease

Figure 11:
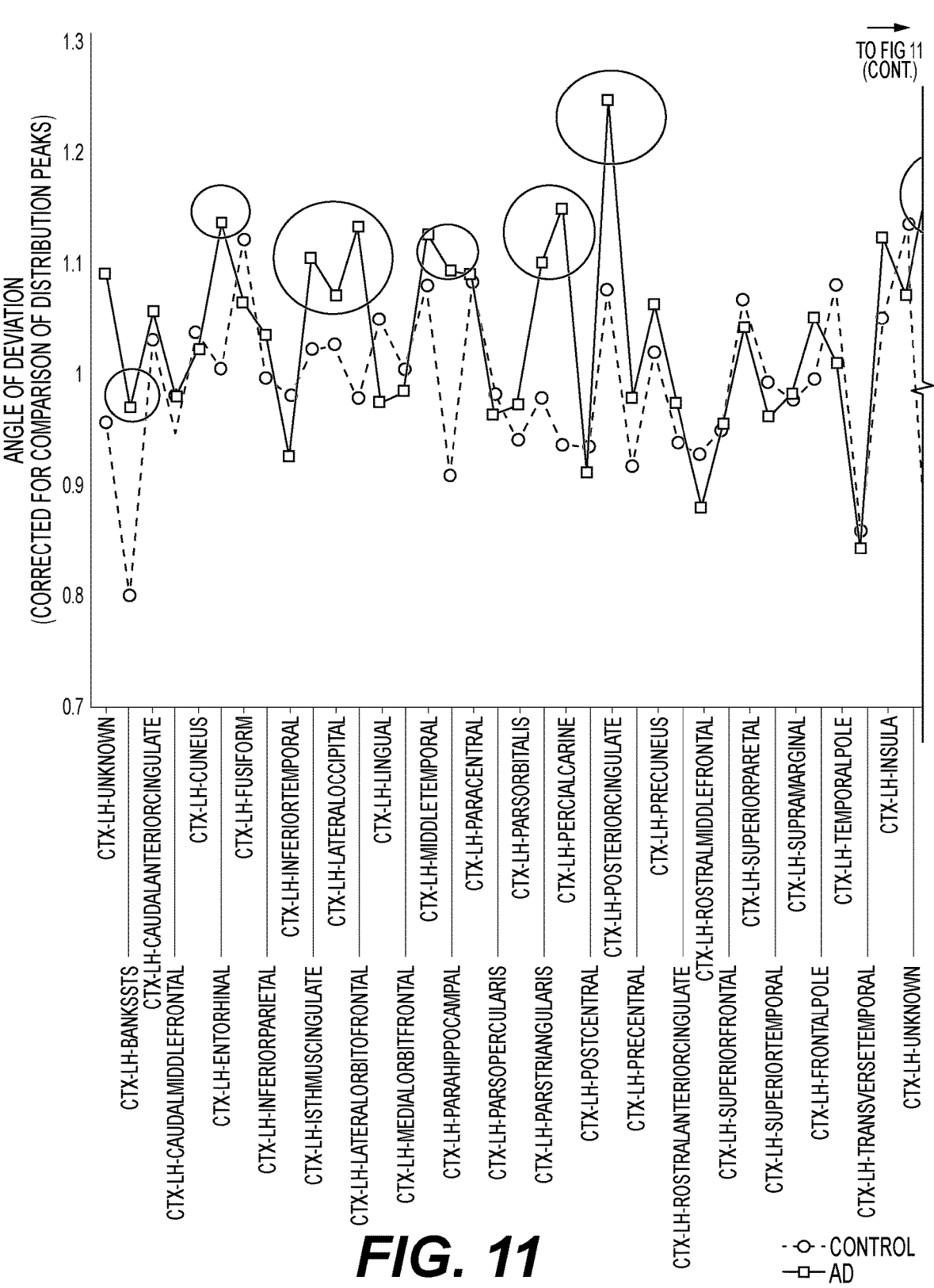
FIG. 11 shows an example of a multi-region analysis of cortical diffusion data from a single control and single AD case with a list of brain regions. Some example regions of interest for differentiating diagnoses are circled.
Figure 11:
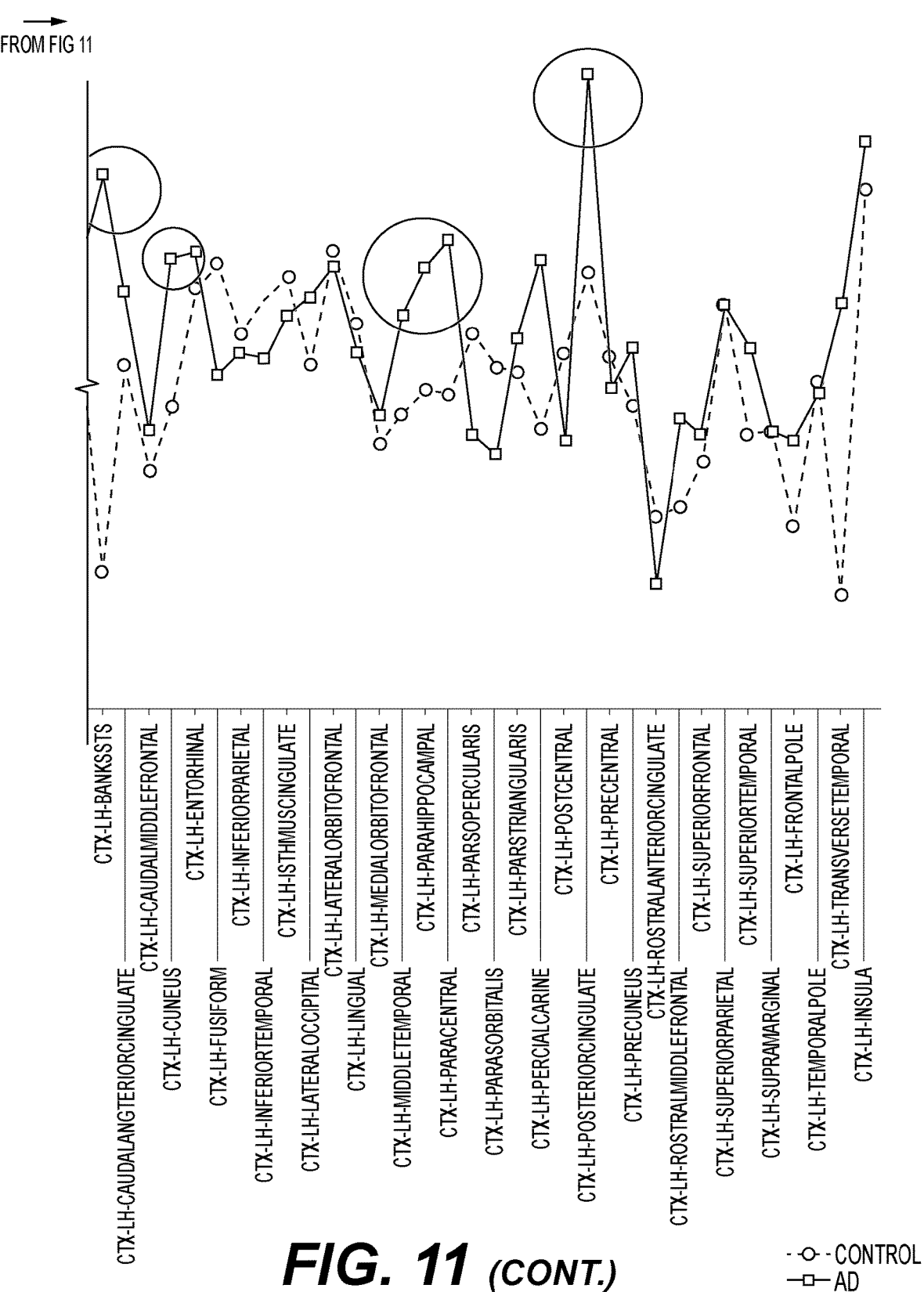

An example of a multi-region analysis of cortical diffusion data from a single control and single AD case with a list of brain regions is shown in FIG. 11. Some example regions of interest for differentiating diagnoses are circled.

Figure 12:
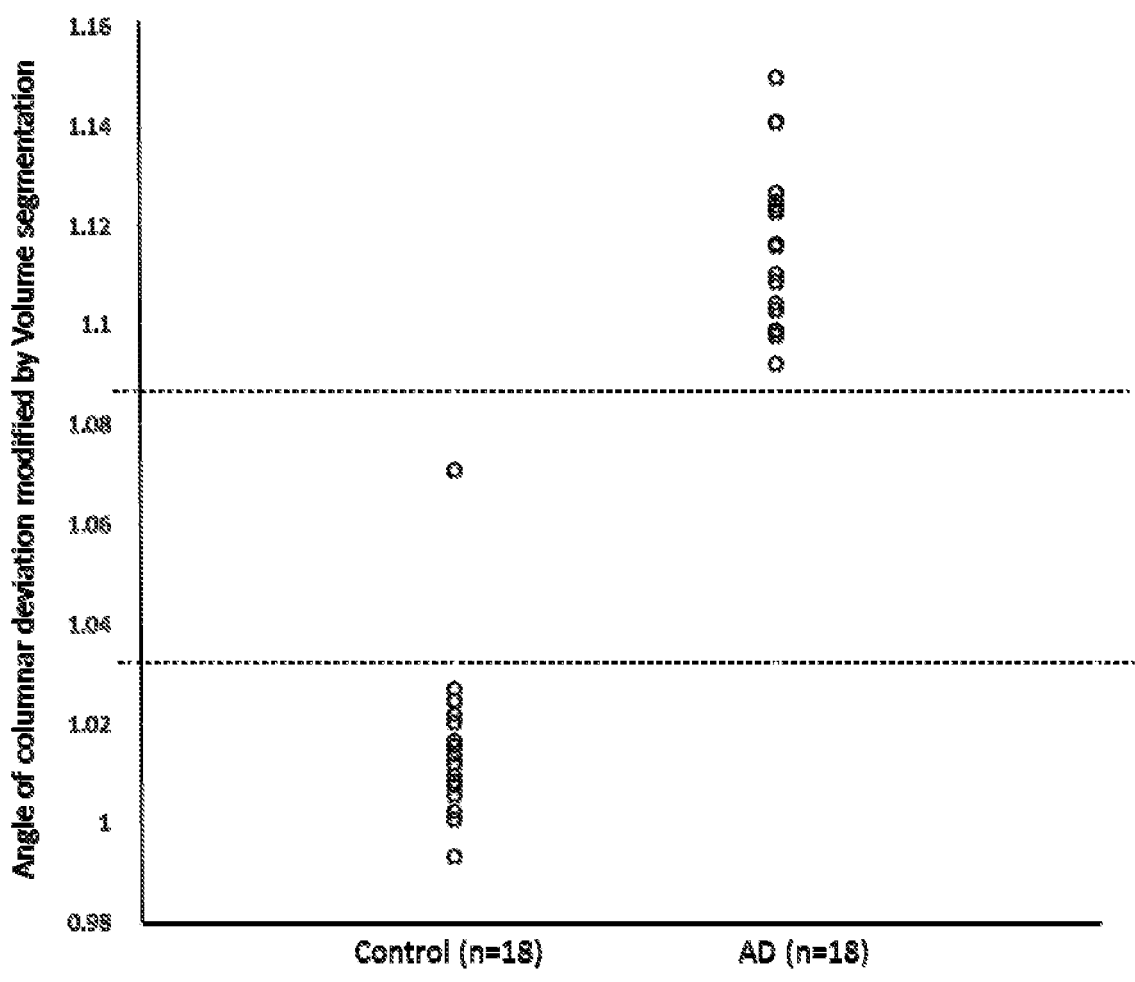
FIG. 12 shows data from an in vivo comparison of 18 AD and 18 control subjects which shows a combination of angle of minicolumnar deviation with volume segmentation data summarised for whole brain. Clear separation of the groups is illustrated with only a single anomalous control case found in the large separation zone delineated by dashed lines.

Data from an in vivo comparison of 18 AD and 18 control subjects is shown in FIG. 12. This shows a combination of angle of minicolumnar deviation with volume segmentation data summarised for whole brain. Clear separation of the groups is illustrated with only a single anomalous control case found in the large separation zone delineated by dashed lines.

Example 5: Diagnosis of Autism Spectrum Disease

Figure 13:
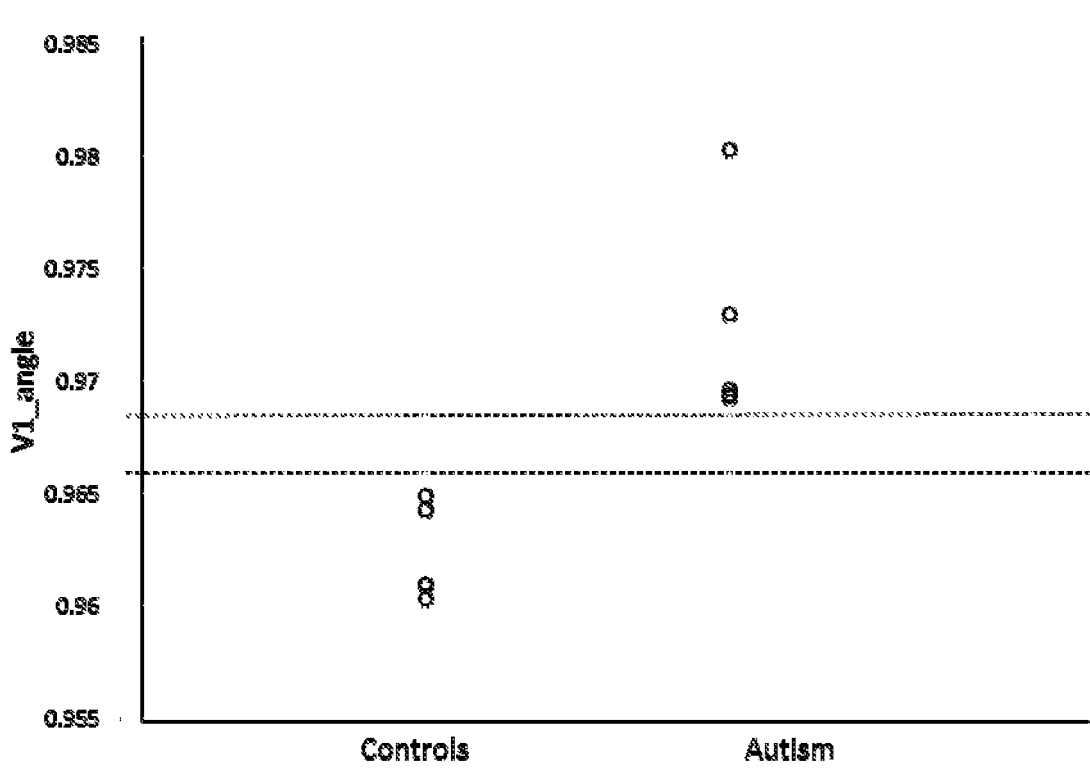
FIG. 13 shows a comparison of in vivo data on autism and controls using one of the new DTI measures related to minicolumn angle of deviation.

A comparison of in vivo data on autism and controls using one of the new DTI measures related to minicolumn angle of deviation is shown in FIG. 13.

The invention claimed is:

1. A computer-implemented method of obtaining an indication of an efficacy of a drug which is being used to treat a cognitive disorder in a subject, the method comprising the steps of:

determining at least one first diffusion Magnetic Resonance Imaging (MRI) measurement of one or more minicolumn-based parameters obtained from cortical grey matter in a brain of the subject;

determining at least one second diffusion MRI measurement of one or more minicolumn-based parameters obtained from the cortical grey matter in the brain of the subject, wherein:

the minicolumn-based parameters are one or more parameters selected from a group consisting of minicolumn width, minicolumn spacing, axonal fibre bundle width, axonal fibre bundle spacing, dendritic fibre bundle width, dendritic fibre bundle spacing, minicolumn core width, and minicolumn peripheral neuropil space, the at least one first diffusion MRI measurement or at least one second diffusion MRI measurement is perpendicular diffusivity, mean minicolumn diffusivity, radial diffusivity, minicolumn width, fractional anisotropy, grey matter density or angle of columnar deviation;

the drug is administered to the subject in an interval between taking of the first and second diffusion MRI measurements, if the first diffusion MRI measurement is positively correlated or proportional to a severity of the cognitive disorder or a trait of said disorder, an increase in the second diffusion MRI measurement compared to the first diffusion MRI measurement is indicative of a lack of efficacy of the drug, and a decrease in the second diffusion MRI measurement compared to the first diffusion MRI measurement is indicative of the efficacy of the drug, and if the first diffusion MRI measurement is negatively correlated or inversely proportional to the severity of the cognitive disorder or a trait of said disorder, an increase in the second diffusion MRI measurement compared to the first diffusion MRI measurement is indicative of the efficacy of the drug, and a decrease in the second diffusion MRI measurement compared to the first diffusion MRI measurement is indicative of the lack of efficacy of the drug.

2. The method as claimed in claim 1, wherein the cognitive disorder is a mental health disorder that affects learning, memory, perception and/or problem solving.

3. The method as claimed in claim 1, wherein the cognitive disorder is a form of dementia.

4. The method as claimed in claim 1, wherein the at least one first diffusion MRI measurement of one or more minicolumn-based parameters or the at least one second diffusion MRI measurement of one or more minicolumn-based parameters are obtained from one or more different regions of the brain, preferably two or more, three or more, four or more, five or more, six or more, seven or more, or eight or more different regions of the brain, most preferably five or more different regions of the brain, or from the whole brain.

5. The method as claimed in claim 1, wherein the at least one first diffusion MRI measurement of one or more minicolumn-based parameters or the at least one second diffusion MRI measurement of one or more minicolumn-based parameters are obtained from or derived from one or more regions or layers of a cortex of the brain, preferably from a cortical layer or cortical layers.

6. The method as claimed in claim 1, wherein the at least one first diffusion MRI measurement of one or more minicolumn-based parameters or the at least one second diffusion MRI measurement of one or more minicolumn-based parameters are obtained from or derived from one or more brain regions selected from the group consisting of parahippocampal gyrus, fusiform gyrus, dorsolateral prefrontal cortex area, Heschl's gyrus, planum temporale, inferior parietal lobule, middle temporal gyrus, a primary visual cortex, an orbitofrontal cortex and a primary motor cortex.

7. The method as claimed in claim 1, wherein the cognitive disorder is Alzheimer's Disease (AD) and wherein the at least one first diffusion MRI measurement of one or more minicolumn-based parameters or the at least one second diffusion MRI measurement of one or more minicolumn-based parameters are obtained from or derived from one or more brain regions selected from the group consisting of:

(i) banks of a superior temporal sulcus, entorhinal, isthmus cingulate, lateral occipital, lateral oribitofrontal, middle temporal, parahippocampal, parstriangularis, pericalcarine or posterior cingulate region of a left-hand cortex; and (ii) the banks of the superior temporal sulcus, cuneus, entorhinal, middle temporal, parahippocampal, paracentral or posterior cingulate region of a right-hand cortex.

8. The method as claimed in claim 1, wherein the cognitive disorder is Alzheimer's Disease (AD) and wherein the at least one first diffusion MRI measurement of one or more minicolumn-based parameters or the at least one second diffusion MRI measurement of one or more minicolumn-based parameters are obtained from or derived from the whole brain.

9. A system or apparatus comprising at least one processing means arranged to carry out the steps of a method as claimed in claim 1.

* * * * *